United States Patent
Schaeffer

(10) Patent No.: US 9,974,674 B2
(45) Date of Patent: May 22, 2018

(54) BRANCH VESSEL PROTHESIS WITH POSITIONAL INDICATOR SYSTEM AND METHOD

(75) Inventor: Darin G. Schaeffer, Bloomington, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 1298 days.

(21) Appl. No.: 10/984,416

(22) Filed: Nov. 8, 2004

(65) Prior Publication Data

US 2007/0179592 A1 Aug. 2, 2007

Related U.S. Application Data

(60) Provisional application No. 60/518,565, filed on Nov. 8, 2003.

(51) Int. Cl.
*A61F 2/954* (2013.01)
*A61F 2/07* (2013.01)
(Continued)

(52) U.S. Cl.
CPC ............... *A61F 2/954* (2013.01); *A61F 2/07* (2013.01); *A61F 2/856* (2013.01); *A61F 2/88* (2013.01);
(Continued)

(58) Field of Classification Search
CPC .... A61F 2/954; A61F 2/07; A61F 2/88; A61F 2/91; A61F 2/856; A61F 2/958;
(Continued)

(56) References Cited

U.S. PATENT DOCUMENTS

| 4,562,596 A | 1/1986 | Kornberg |
| 4,665,918 A | 5/1987 | Garza et al. |

(Continued)

FOREIGN PATENT DOCUMENTS

| EP | 0 461 791 B1 | 6/1991 |
| EP | 0 646 365 B1 | 9/1994 |

(Continued)

OTHER PUBLICATIONS

International Search Report for PCT/US2004/037538 dated Apr. 4, 2005.

(Continued)

*Primary Examiner* — Richard Louis
(74) *Attorney, Agent, or Firm* — Brinks Gilson & Lione

(57) ABSTRACT

A stent graft system for intraluminal deployment in an aorta and a branch vessel includes an aorta stent graft with a fenestration aligned with a branch vessel and a branch vessel prosthesis with a flaring portion at a proximal end and a tubular portion. When deployed, the flaring portion of the branch vessel prosthesis is retained within the aorta stent graft, and the tubular portion extends through the fenestration and into the branch vessel. The system includes at least one positional indicator, including a positional indicator associated with the branch vessel prosthesis for indicating the position of a point along the branch vessel prosthesis predetermined for optimal alignment with the fenestration during deployment.

18 Claims, 17 Drawing Sheets

(51) Int. Cl.

| | | |
|---|---|---|
| *A61F 2/856* | (2013.01) | |
| *A61F 2/88* | (2006.01) | |
| *A61F 2/91* | (2013.01) | |
| *A61F 2/915* | (2013.01) | |
| *A61F 2/958* | (2013.01) | |
| *A61B 17/11* | (2006.01) | |
| *A61F 2/06* | (2013.01) | |
| *A61F 2/82* | (2013.01) | |
| *A61F 2/848* | (2013.01) | |
| *A61F 2/95* | (2013.01) | |
| *A61F 2/89* | (2013.01) | |

(52) U.S. Cl.
CPC ............... *A61F 2/91* (2013.01); *A61F 2/915* (2013.01); *A61F 2/958* (2013.01); *A61B 2017/1107* (2013.01); *A61B 2017/1139* (2013.01); *A61F 2/064* (2013.01); *A61F 2/89* (2013.01); *A61F 2002/065* (2013.01); *A61F 2002/067* (2013.01); *A61F 2002/075* (2013.01); *A61F 2002/821* (2013.01); *A61F 2002/8483* (2013.01); *A61F 2002/8486* (2013.01); *A61F 2002/91508* (2013.01); *A61F 2002/91525* (2013.01); *A61F 2002/91533* (2013.01); *A61F 2002/91558* (2013.01); *A61F 2002/91566* (2013.01); *A61F 2002/9511* (2013.01); *A61F 2210/0076* (2013.01); *A61F 2220/005* (2013.01); *A61F 2220/0016* (2013.01); *A61F 2220/0075* (2013.01); *A61F 2220/0083* (2013.01); *A61F 2230/005* (2013.01); *A61F 2230/0054* (2013.01); *A61F 2230/0067* (2013.01); *A61F 2230/0078* (2013.01); *A61F 2250/0018* (2013.01); *A61F 2250/0039* (2013.01); *A61F 2250/0097* (2013.01); *A61F 2250/0098* (2013.01)

(58) Field of Classification Search
CPC .... A61F 2/915; A61F 2/89; A61F 2220/0075; A61F 2210/0076; A61F 2250/0098; A61F 2002/8486; A61F 2250/0097
USPC .................................................. 623/1.11, 1.12
See application file for complete search history.

(56) References Cited

U.S. PATENT DOCUMENTS

| | | |
|---|---|---|
| 4,950,227 A | 8/1990 | Savin et al. |
| 4,957,508 A | 9/1990 | Kaneko et al. |
| 5,104,404 A | 4/1992 | Wolff |
| 5,123,917 A | 6/1992 | Lee |
| 5,387,235 A | 2/1995 | Chuter |
| 5,409,495 A | 4/1995 | Osborn |
| 5,447,497 A | 9/1995 | Sogard et al. |
| 5,522,880 A | 6/1996 | Barone et al. |
| 5,552,880 A | 6/1996 | Barone et al. |
| 5,571,173 A | 11/1996 | Parodi |
| 5,578,071 A | 11/1996 | Parodi |
| 5,591,229 A | 1/1997 | Parodi |
| 5,607,444 A | 3/1997 | Lam |
| 5,617,878 A | 4/1997 | Taheri |
| 5,632,762 A | 5/1997 | Myler |
| 5,653,743 A | 8/1997 | Martin |
| 5,693,084 A | 12/1997 | Parodi |
| 5,693,087 A | 12/1997 | Parodi |
| 5,720,776 A | 2/1998 | Chuter et al. |
| 5,755,778 A | 5/1998 | Kleshinski |
| 5,851,228 A | 12/1998 | Pinheiro |
| 5,921,995 A | 7/1999 | Kleshinski |
| 5,957,974 A | 9/1999 | Thompson et al. |
| 5,961,548 A | 10/1999 | Shmulewitz |
| 5,980,531 A * | 11/1999 | Goodin et al. ............. 623/1.11 |
| 5,984,955 A | 11/1999 | Wisselink |
| 6,010,530 A | 1/2000 | Goicoechea |
| 6,030,414 A | 2/2000 | Taheri |
| 6,036,697 A | 3/2000 | DiCaprio |
| 6,053,941 A | 4/2000 | Lindenberg et al. |
| 6,056,700 A * | 5/2000 | Burney ................. A61B 90/39 600/564 |
| 6,059,824 A | 5/2000 | Taheri |
| 6,074,416 A | 6/2000 | Berg et al. |
| 6,077,296 A | 6/2000 | Shokoohi et al. |
| 6,096,071 A * | 8/2000 | Yadav .......................... 623/1.15 |
| 6,102,940 A | 8/2000 | Robichon et al. |
| 6,152,944 A | 11/2000 | Holman et al. |
| 6,152,956 A | 11/2000 | Pierce |
| 6,168,621 B1 | 1/2001 | Vrba |
| 6,171,329 B1 | 1/2001 | Shaw et al. |
| 6,176,875 B1 | 1/2001 | Lenker et al. |
| 6,187,014 B1 * | 2/2001 | Goodin .................. A61F 2/958 604/101.02 |
| 6,187,033 B1 | 2/2001 | Schmitt et al. |
| 6,206,931 B1 | 3/2001 | Cook et al. |
| 6,210,429 B1 * | 4/2001 | Vardi ..................... A61F 2/856 606/153 |
| 6,217,609 B1 | 4/2001 | Haverkost |
| 6,221,090 B1 | 4/2001 | Wilson |
| 6,238,430 B1 | 5/2001 | Klumb et al. |
| 6,290,728 B1 | 9/2001 | Phelps et al. |
| 6,290,731 B1 | 9/2001 | Solovay et al. |
| 6,293,966 B1 * | 9/2001 | Frantzen ..................... 623/1.15 |
| 6,325,819 B1 | 12/2001 | Pavenik et al. |
| 6,325,826 B1 | 12/2001 | Vardi et al. |
| 6,334,869 B1 | 1/2002 | Leonhardt et al. |
| 6,344,056 B1 | 2/2002 | Dehdashtian |
| 6,395,018 B1 | 5/2002 | Castaneda |
| 6,398,803 B1 | 6/2002 | Layne et al. |
| 6,409,756 B1 | 6/2002 | Murphy |
| 6,409,757 B1 | 6/2002 | Trout, III et al. |
| 6,428,565 B1 | 8/2002 | Wisselink |
| 6,451,050 B1 | 9/2002 | Rudakov et al. |
| 6,471,672 B1 | 10/2002 | Brown et al. |
| 6,482,227 B1 | 11/2002 | Solovay |
| 6,517,574 B1 | 2/2003 | Chuter |
| 6,520,988 B1 | 2/2003 | Colombo et al. |
| 6,524,335 B1 | 2/2003 | Hartley et al. |
| 6,527,799 B2 | 3/2003 | Shanley |
| 6,572,648 B1 | 6/2003 | Klumb et al. |
| 6,582,394 B1 | 6/2003 | Reiss et al. |
| 6,585,758 B1 | 7/2003 | Chouinard et al. |
| 6,616,675 B1 | 9/2003 | Evard et al. |
| 6,645,242 B1 | 11/2003 | Quinn |
| 6,652,567 B1 | 11/2003 | Deaton |
| 6,663,667 B2 | 12/2003 | Dehdashtian et al. |
| 6,669,720 B1 | 12/2003 | Pierce |
| 6,692,483 B2 * | 2/2004 | Vardi et al. ................... 604/529 |
| 6,695,877 B2 | 2/2004 | Brucker et al. |
| 6,706,062 B2 | 3/2004 | Vardi et al. |
| 6,723,116 B2 | 4/2004 | Taheri |
| 6,733,523 B2 | 5/2004 | Shaolian et al. |
| 6,773,522 B2 | 5/2004 | Schmitt et al. |
| 6,767,358 B2 | 7/2004 | Leonhardt et al. |
| 6,773,457 B2 | 8/2004 | Ivancev et al. |
| 6,814,752 B1 | 11/2004 | Chuter |
| 2001/0027338 A1 | 10/2001 | Greenberg |
| 2001/0029396 A1 * | 10/2001 | Wilson .................. A61F 2/856 623/1.11 |
| 2002/0052648 A1 | 5/2002 | McGuckin, Jr. et al. |
| 2002/0072790 A1 | 6/2002 | McGuckin, Jr. et al. |
| 2002/0082684 A1 | 6/2002 | Mishaly |
| 2002/0099441 A1 | 7/2002 | Dehdashtian |
| 2002/0144696 A1 | 10/2002 | Sharkawy et al. |
| 2002/0156517 A1 | 10/2002 | Perouse |
| 2002/0156522 A1 | 10/2002 | Ivancev et al. |
| 2002/0193872 A1 | 12/2002 | Trout, III et al. |
| 2002/0198585 A1 | 12/2002 | Wisselink |
| 2003/0033005 A1 | 2/2003 | Houser et al. |
| 2003/0069630 A1 * | 4/2003 | Burgermeister .......... A61F 2/91 623/1.15 |
| 2003/0074050 A1 | 4/2003 | Kerr |
| 2003/0093145 A1 | 5/2003 | Lawrence-Brown et al. |

(56) References Cited

U.S. PATENT DOCUMENTS

| | | | |
|---|---|---|---|
| 2003/0120333 A1 | 6/2003 | Ouriel et al. | |
| 2003/0130720 A1 | 7/2003 | De Palma et al. | |
| 2003/0130724 A1 | 7/2003 | De Palma et al. | |
| 2003/0139796 A1* | 7/2003 | Sequin | A61F 2/915 623/1.12 |
| 2003/0199967 A1 | 10/2003 | Hartley et al. | |
| 2003/0199973 A1 | 10/2003 | Chuter et al. | |
| 2003/0220682 A1 | 11/2003 | Kujawski | |
| 2003/0225453 A1 | 12/2003 | Murch | |
| 2003/0233140 A1 | 12/2003 | Hartley et al. | |
| 2004/0106972 A1 | 1/2004 | Deaton | |
| 2004/0024446 A1 | 2/2004 | Smith | |
| 2004/0034406 A1 | 2/2004 | Thramann | |
| 2004/0044396 A1 | 3/2004 | Clerc et al. | |
| 2004/0044399 A1* | 3/2004 | Ventura | A61F 2/91 623/1.16 |
| 2004/0054396 A1 | 3/2004 | Hartley et al. | |
| 2004/0059406 A1 | 3/2004 | Cully et al. | |
| 2004/0073288 A1 | 4/2004 | Kerr | |
| 2004/0093078 A1 | 5/2004 | Moll et al. | |
| 2004/0098079 A1 | 5/2004 | Hartley et al. | |
| 2004/0117004 A1 | 6/2004 | Osborne et al. | |
| 2004/0133266 A1 | 7/2004 | Clerc et al. | |
| 2004/0138737 A1 | 7/2004 | Davidons et al. | |
| 2004/0167307 A1 | 8/2004 | Frantzen | |
| 2004/0167607 A1 | 8/2004 | Frantzen | |
| 2004/0254627 A1* | 12/2004 | Thompson et al. | 623/1.11 |
| 2005/0049678 A1 | 3/2005 | Cocks et al. | |
| 2005/0102021 A1 | 5/2005 | Osborne | |
| 2005/0288769 A1* | 12/2005 | Globerman | A61F 2/91 623/1.15 |

FOREIGN PATENT DOCUMENTS

| | | |
|---|---|---|
| EP | 0 903 118 A2 | 9/1994 |
| EP | 2 065 015 | 6/2009 |
| JP | 404231954 A | 8/1992 |
| JP | 407008512 A | 1/1995 |
| WO | WO 98/53761 | 12/1998 |
| WO | WO 02/067815 | 9/2002 |
| WO | WO03/020173 A1 | 3/2003 |
| WO | WO 03/034948 | 5/2003 |
| WO | WO 03/053287 | 7/2003 |
| WO | WO 03/065933 | 8/2003 |
| WO | WO 03/082153 | 10/2003 |
| WO | WO 2005/034807 | 4/2005 |

OTHER PUBLICATIONS

Restriction Requirement for U.S. Appl. No. 10/984,040 dated Apr. 28, 2009, 9 pages.
Response to Restriction Requirement for U.S. Appl. No. 10/984,040 dated May 21, 2009, 10 pages.
Restriction Requirement for U.S. Appl. No. 10/984,040 dated Aug. 3, 2009, 6 pages.
Interview Summary for U.S. Appl. No. 10/984,040 dated Oct. 9, 2009, 4 pages.
Office Action for U.S. Appl. No. 10/984,040 dated Jan. 29, 2010, 10 pages.
Final Rejection for U.S. Appl. No. 10/984,167 dated Jun. 1, 2009, 8 pages.
Amendment After Final Rejection for U.S. Appl. No. 10/984,167 dated Aug. 3, 2009, 11 pages.
Advisory Action for U.S. Appl. No. 10/984,167 dated Aug. 13, 2009, 3 pages.
Pre-Appeal Brief Request for U.S. Appl. No. 10/984,167 dated Sep. 1, 2009, 12 pages.
Decision from Pre-Appeal Brief Review for U.S. Appl. No. 10/984,167 dated Nov. 24, 2009, 2 pages.
Amendment After Non-Final Rejection for U.S. Appl. No. 10/984,131 dated May 5, 2009, 19 pages.
Final Rejection for U.S. Appl. No. 10/984,131 dated Jul. 24, 2009, 9 pages.
Amendment After Final Rejection for U.S. Appl. No. 10/984,131 dated Sep. 24, 2009, 14 pages.
Advisory Action for U.S. Appl. No. 10/984,131 dated Oct. 5, 2009, 3 pages.
Pre-Appeal Brief Request for U.S. Appl. No. 10/984,131 dated Oct. 26, 2009, 12 pages.
Decision from Pre-Appeal Brief Review for U.S. Appl. No. 10/984,131 dated Dec. 23, 2009, 2 pages.
Final Rejection for U.S. Appl. No. 10/984,417 dated Jul. 29, 2009, 11 pages.
Telephone Interview Summary for U.S. Appl. No. 10/984,417 dated Nov. 16, 2009, 4 pages.
Supplemental Final Rejection for U.S. Appl. No. 10/984,417 dated Nov. 20, 2009, 13 pages.
Amendment After Non-Final Rejection for U.S. Appl. No. 10/984,520 dated May 11, 2009, 21 pages.
Final Rejection for U.S. Appl. No. 10/984,520 dated Aug. 17, 2009, 7 pages.
Written Opinion for PCT/US2004/37538 dated Apr. 4, 2005, 6 pages.
International Preliminary Report on Patentability for PCT/US2004/37538 dated May 8, 2006, 7 pages.
Office Action for European Patent Application No. 04818690.2 dated Dec. 7, 2009, 3 pages.
Response to Office Action for European Patent Application No. 04818690.2 dated Mar. 15, 2010, 10 pages.
Office Action for European Patent Application No. 04818690.2 dated Dec. 4, 2014, 5 pages.
Office Action for U.S. Appl. No. 10/984,040 dated May 7, 2007, 8 pages.
Amendment After Non-Final Rejection for U.S. Appl. No. 10/984,040 dated Sep. 6, 2007, 12 pages.
Office Action for U.S. Appl. No. 10/984,040 dated Nov. 16, 2007, 5 pages.
Amendment After Non-Final Rejection for U.S. Appl. No. 10/984,040 dated Feb. 18, 2008, 12 pages.
Final Office Action for U.S. Appl. No. 10/984,040 dated May 1, 2008, 9 pages.
Request for Continued Examination and Amendment for U.S. Appl. No. 10/984,040 dated Sep. 30, 2008, 22 pages.
Office Action for U.S. Appl. No. 10/984,040 dated Oct. 30, 2008, 6 pages.
Office Action for U.S. Appl. No. 10/984,167 dated Nov. 16, 2006, 13 pages.
Amendment After Non-Final Rejection for U.S. Appl. No. 10/984,167 dated Feb. 15, 2007, 11 pages.
Final Office Action for U.S. Appl. No. 10/984,167 dated Apr. 27, 2007, 11 pages.
Amendment After Final for U.S. Appl. No. 10/984,167 dated Aug. 27, 2007, 16 pages.
Advisory Action for U.S. Appl. No. 10/984,167 dated Sep. 18, 2007, 3 pages.
Request for Continued Examination and Amendment for U.S. Appl. No. 10/984,167 dated Sep. 27, 2007, 15 pages.
Office Action for U.S. Appl. No. 10/984,167 dated Oct. 30, 2007, 10 pages.
Amendment After Non-Final Rejection for U.S. Appl. No. 10/984,167 dated Jan. 28, 2008, 12 pages.
Final Office Action for U.S. Appl. No. 10/984,167 dated Apr. 22, 2008, 9 pages.
Request for Continued Examination and Amendment for U.S. Appl. No. 10/984,167 dated Sep. 22, 2008, 19 pages.
Office Action for U.S. Appl. No. 10/984,167 dated Nov. 28, 2008, 10 pages.
Office Action for U.S. Appl. No. 10/984,131 dated Nov. 16, 2006, 12 pages.
Amendment After Non-Final Rejection for U.S. Appl. No. 10/984,131 dated Mar. 16, 2007, 10 pages.
Final Office Action for U.S. Appl. No. 10/984,131 dated Jun. 22, 2007, 12 pages.

(56) References Cited

OTHER PUBLICATIONS

Amendment After Final for U.S. Appl. No. 10/984,131 dated Aug. 22, 2007, 13 pages.
Advisory Action for U.S. Appl. No. 10/984,131 dated Sep. 18, 2007, 3 pages.
Request for Continued Examination and Amendment for U.S. Appl. No. 10/984,131 dated Sep. 28, 2007, 19 pages.
Office Action for U.S. Appl. No. 10/984,131 dated Dec. 12, 2007, 13 pages.
Amendment After Non-Final Rejection for U.S. Appl. No. 10/984,131 dated Apr. 14, 2008, 30 pages.
Final Office Action for U.S. Appl. No. 10/984,131 dated Aug. 14, 2008, 14 pages.
Request for Continued Examination and Amendment for U.S. Appl. No. 10/984,131 dated Oct. 13, 2008, 20 pages.
Office Action for U.S. Appl. No. 10/984,131 dated Jan. 5, 2009, 10 pages.
Office Action for U.S. Appl. No. 10/984,417 dated Nov. 16, 2006, 12 pages.
Amendment After Non-Final Rejection for U.S. Appl. No. 10/984,417 dated Feb. 13, 2007, 13 pages.
Final Office Action for U.S. Appl. No. 10/984,417 dated May 7, 2007, 14 pages.
Amendment After Final for U.S. Appl. No. 10/984,417 dated Aug. 10, 2007, 19 pages.
Request for Continued Examination and Amendment for U.S. Appl. No. 10/984,417 dated Oct. 23, 2007, 19 pages.
Restriction Requirement for U.S. Appl. No. 10/984,417 dated Jan. 8, 2008, 6 pages.
Response to Restriction/Election Requirement for U.S. Appl. No. 10/984,417 dated Jan. 31, 2008, 8 pages.
Reply to Notice of Non-Compliant Amendment for U.S. Appl. No. 10/984,417 dated Mar. 7, 2008, 14 pages.
Office Action for U.S. Appl. No. 10/984,417 dated Jun. 26, 2008, 16 pages.
Amendment After Non-Final Rejection for U.S. Appl. No. 10/984,417 dated Sep. 26, 2008, 15 pages.
Reply to Notice of Non-Compliant Amendment for U.S. Appl. No. 10/984,417 dated Nov. 3, 2008, 15 pages.
Office Action for U.S. Appl. No. 10/984,520 dated Nov. 27, 2006, 16 pages.
Amendment After Non-Final Rejection for U.S. Appl. No. 10/984,520 dated Feb. 27, 2007, 17 pages.
Final Office Action for U.S. Appl. No. 10/984,520 dated May 15, 2007, 10 pages.
Amendment After Final for U.S. Appl. No. 10/984,520 dated Aug. 15, 2007, 11 pages.
Advisory Action for U.S. Appl. No. 10/984,520 dated Sep. 6, 2007, 3 pages.
Request for Continued Examination and Amendment for U.S. Appl. No. 10/984,520 dated Oct. 15, 2007, 16 pages.
Office Action for U.S. Appl. No. 10/984,520 dated Dec. 28, 2007, 8 pages.
Amendment After Non-Final Rejection for U.S. Appl. No. 10/984,520 dated Mar. 28, 2008, 11 pages.
Final Office Action for U.S. Appl. No. 10/984,520 dated Jun. 23, 2008, 9 pages.
Request for Continued Examination for U.S. Appl. No. 10/984,520 dated Sep. 22, 2008, 20 pages.
Office Action for U.S. Appl. No. 10/984,520 dated Dec. 9, 2008, 8 pages.

\* cited by examiner

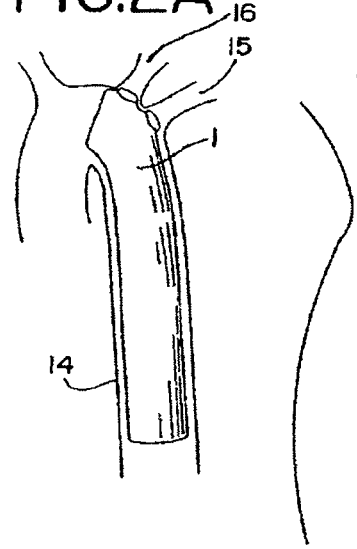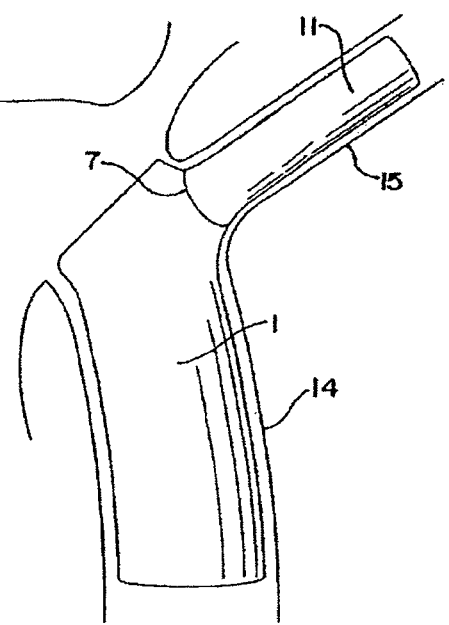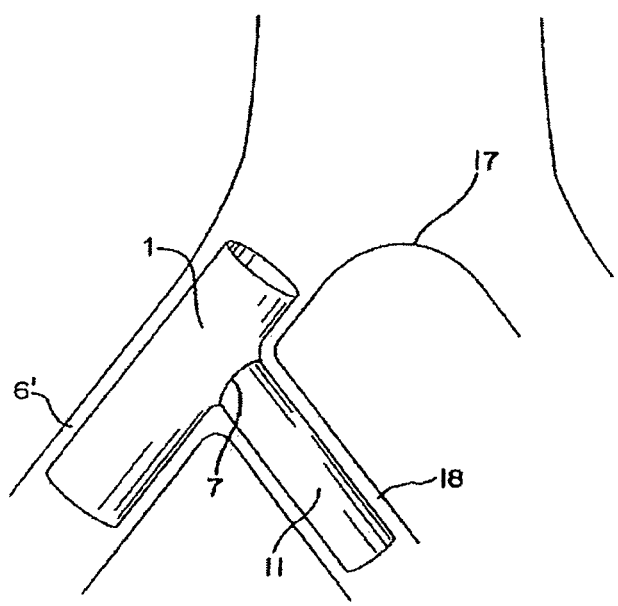

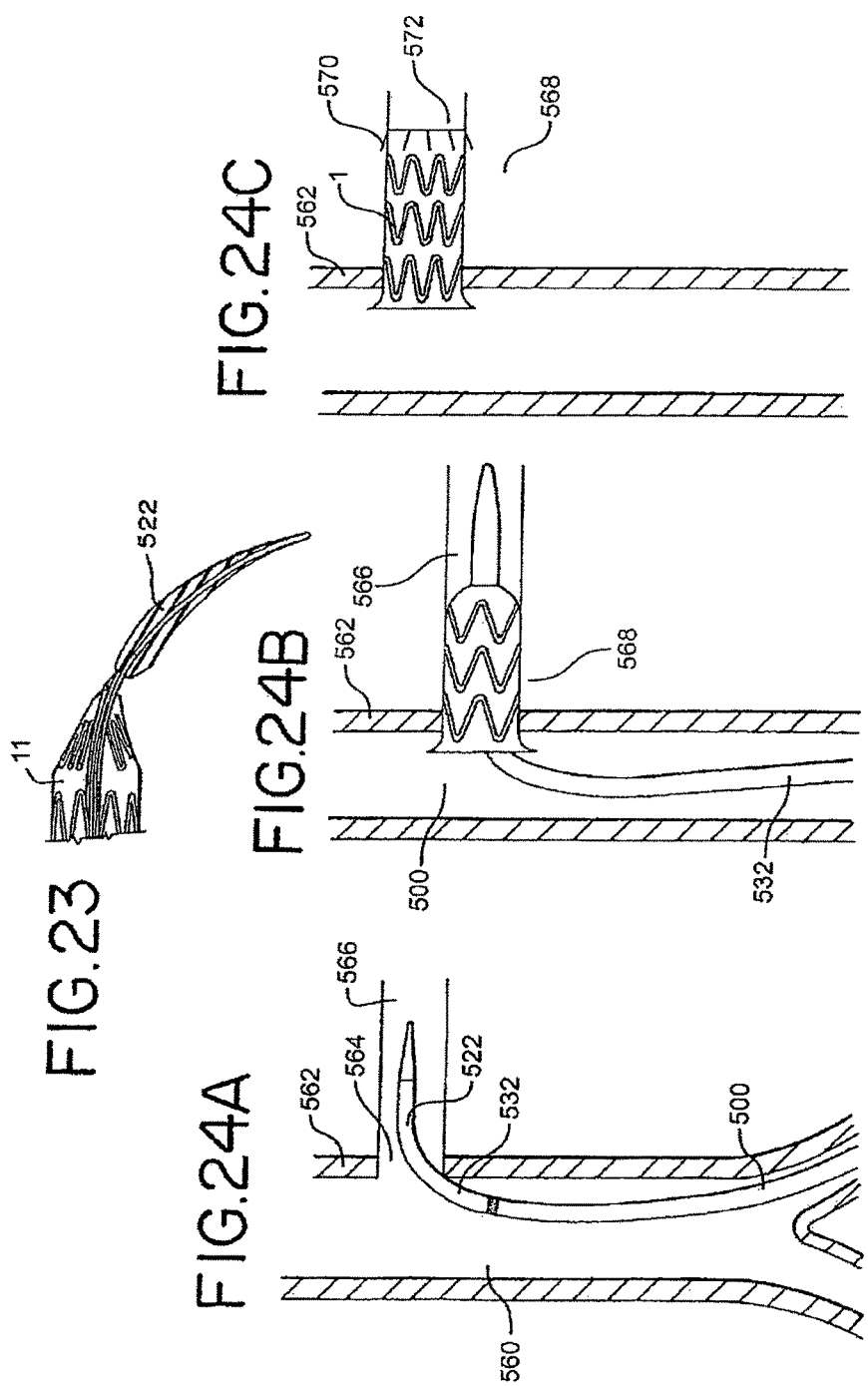

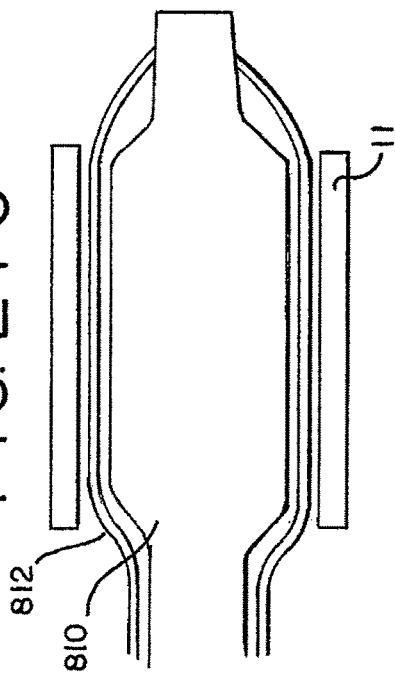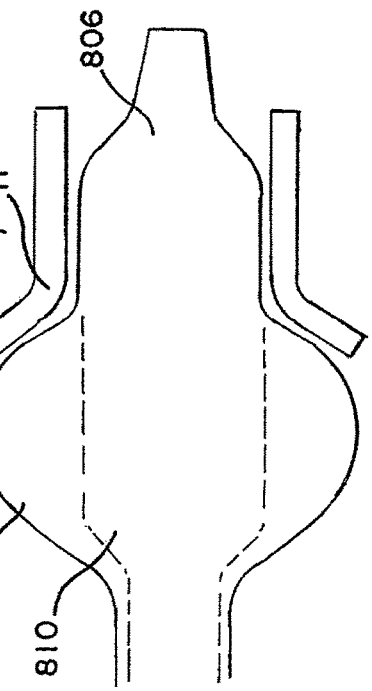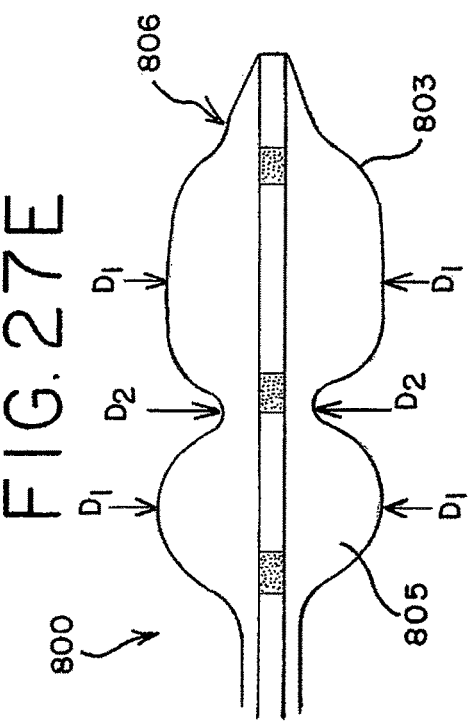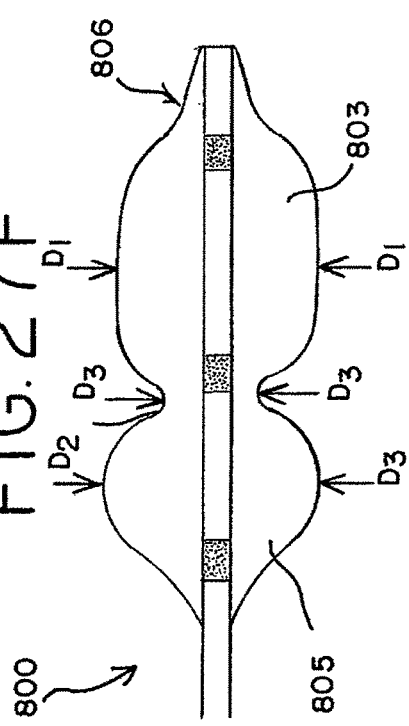

BRANCH VESSEL PROTHESIS WITH POSITIONAL INDICATOR SYSTEM AND METHOD

RELATED APPLICATIONS

This application claims priority to provisional application No. 60/518,565 filed on Nov. 8, 2003, the entire disclosure of which is incorporated by reference herein.

TECHNICAL FIELD

This invention relates to medical devices and more particularly, to endoluminal devices suitable for various medical applications and the methods for making and using such endoluminal devices.

BACKGROUND

The functional vessels of human and animal bodies, such as blood vessels and ducts, occasionally weaken or even rupture. For example, an aortic wall can weaken, resulting in an aneurysm. Upon further exposure to hemodynamic forces, such an aneurysm can rupture. In Western European and Australian men who are between 60 and 75 years of age, aortic aneurysms greater than 29 mm in diameter are found in 6.9% of the population, and those greater than 40 mm are present in 1.8% of the population.

One intervention for weakened, aneurismal, dissected or ruptured vessels is the use of an endoluminal device or prosthesis such as a stent graft to provide some or all of the functionality of the original, healthy vessel and/or preserve any remaining vascular integrity by replacing a length of the existing vessel wall that contains the site of vessel weakness or failure. Stent grafts for endoluminal deployment are generally formed from a tube of a biocompatible material in combination with one or more stents to maintain a lumen therethrough. Stent grafts effectively exclude the defect by sealing both proximally and distally to the defect, and shunting blood through its length. A device of this type can, for example, treat various arterial aneurysms, including those in the thoracic aorta or abdominal aorta.

A bifurcated stent graft, one example of an endoluminal prosthesis, is known for use in treating abdominal aortic aneurysms, where the stent graft at the proximal end defines a single lumen for placement within the aorta and at the other end bifurcates into the iliac arteries. One such stent graft, disclosed in PCT application WO98/53761, is useful for repair of abdominal aortic aneurysms. That application discloses a stent graft that includes a sleeve or tube of biocompatible graft material such as woven polyester fabric or polytetrafluoroethylene (PTFE) defining a main lumen and two iliac limbs. The stent graft further includes several stents secured therealong. The stent graft is designed to span an aneurysm that extends along the aorta between the iliac and renal arteries. Unbifurcated stent grafts, in which the distal portion extends into only one iliac artery in treating an abdominal aorta, or which are used to treat the thoracic aorta are also used.

In the WO98/53761 application, the fabric-covered portion of the single-lumen proximal end of the stent graft bears against the wall of the aorta above the aneurysm and distal to the renal arteries to seal off the aneurysm. Thin wire struts of a juxtarenal attachment stent traverse the renal artery ostia without occluding them. Barbs on the attachment stent help anchor the stent graft in place.

One stent graft approved by the Food and Drug Administration (FDA) to treat aortic aneurysms is the ZENITH® AAA Endovascular Graft (Cook Incorporated, Bloomington, Ind.). The ZENITH® AAA Endovascular Graft is made up of three prosthetic modules: a bifurcated main body module and two leg modules. The main body is positioned in the aorta. The legs are positioned in the iliac arteries and connect to the main body. The stent graft thus extends from a section of the aorta, typically below the renal arteries and into both iliac arteries. The graft material is made of a woven polyester fabric like that used in open surgical repair. Standard surgical suturing techniques are used to sew the graft material to a frame of stainless steel stents. These self-expanding stents provide support for the graft material.

An endoluminal prosthesis may be comprised of multiple prosthetic modules. A modular prosthesis allows a surgeon to accommodate a wide variation in vessel morphology while reducing the necessary inventory of differently sized prostheses. For example, aortas vary in length, diameter and angulation between the renal artery region and the region of the aortic bifurcation. Prosthetic modules that fit each of these variables can be assembled to form a prosthesis, obviating the need for a custom prosthesis or large inventories of prostheses that accommodate all possible combinations of these variables. A modular system may also accommodate deployment options by allowing the proper placement of one module before the implantation of an adjoining module.

Modular prostheses are typically assembled in situ by overlapping the tubular ends of the prosthetic modules so that the end of one module sits partially inside the other module, preferably forming circumferential apposition through the overlap region. This attachment process is called "telescoping." The connections between prosthetic modules are typically maintained by the friction forces at the overlap region and enhanced by the radial force exerted by the internal prosthetic module on the external prosthetic modules where the two overlap. The fit may be further enhanced by stents attached to the modules at the overlap region.

In many cases, however, the damaged or defected portion of the vasculature may include a branch vessel. For example, in the case of the abdominal aorta, there are at least three branch vessels, including the celiac, mesenteric, and renal arteries, leading to various other body organs. Thus, when the damaged portion of the vessel includes one or more of these branch vessels, some accommodation must be made to ensure that the stent graft does not block or hinder blood flow through the branch vessel.

Attempts to maintain blood flow to branch vessels have included providing one or more fenestrations or holes in the side wall of the stent graft. Other attempts have included providing a stent graft in which the branch vessel portion of the vessel is spanned by wires or the like. These devices have been used to treat diseased vessels, such as abdominal aortic aneurysms within the aorta that extend to or above the renal, celiac and/or mesenteric arteries. Generally, this treatment involves aligning the fenestrations with the branch vessels, which may extend approximately at right angles on both sides from the aorta.

In many cases, the vasculature is not symmetric. In addition, even with symmetrical vasculature, physiological forces may cause a previously placed branch vessel stent graft to shift causing the position of the fenestration with respect to the branch vessel to become offset. In other instances, the diseased vasculature may extend into the branch vessel and affects the ostium of the branch vessel. In some circumstances the branch vessel stent graft deployed within the main vessel may not properly seal and secure to the branch vessel and lead to leaks (endoleaks) between the branch vessel stent graft and the main vessel, a reduced blood flow to the branch vessels, and/or obscure access to portions of the branch vessel, necessitating further interventional procedures.

When treating a vessel with an endoluminal prosthesis, it may therefore be preferable to preserve the original circulation by providing a prosthetic branch that extends from the prosthesis to a side branch vessel so that the blood flow into the branch vessel is not impeded. For example, the aortic section of the ZENITH® abdominal aortic stent graft (Cook Incorporated, Bloomington, Ind.), described above, can be designed to extend above the renal arteries, and/or the celiac or mesenteric arteries, and to have prosthetic side branches that extend into the renal arteries. Branch vessel prostheses can form a connection to an aortic stent graft through fenestrations in the stent graft to complete the prosthesis. Furthermore, some aneurysms extend into the branch vessels in both the thoracic and abdominal aorta. Deploying prostheses with prosthetic branches into these vessels may help prevent expansion and/or rupture of these aneurysms.

In other situations, it may not be necessary to form a lumen that extends into the branch vessel, i.e. a stent graft. Instead, it may only be necessary to maintain patency of the branch vessel by propping the walls of the branch vessel open, also known as "stenting." In these situations, the branch vessel prosthesis can be a mere stent, also known as an "open stent" or "bare stent."

Thus, there remains a need for a device a branch vessel stent or stent graft to secure and seal the branch vessel stent graft to a branch vessel and within a fenestrated device.

SUMMARY

This application relates to a branch vessel stent for use in connection with a fenestrated stent graft device for placement in a vessel of a body.

In particular, this application relates to stent graft system for intraluminal deployment in an aorta and a branch vessel including an aorta stent graft with a fenestration aligned with a branch vessel, a branch vessel prosthesis, preferably a stent graft, with a flaring portion at a proximal end and a tubular portion, wherein, when deployed, the flaring portion is retained within the aorta stent graft, and the tubular portion extends through the fenestration and into the branch vessel; and a positional indicator associated with the branch vessel prosthesis for indicating the position of a point along the branch vessel stent graft predetermined for optimal alignment with the fenestration during deployment. The system may include additional positional indicators for indicating other points along the branch vessel prosthesis or the aorta stent graft.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 2A illustrates a stent graft positioned in the thoracic aorta and having fenestrations aligned with the left subclavian artery and the left common carotid artery.

FIG. 2B shows the aorta stent graft of FIG. 2A with a branch vessel prosthesis extending into the subclavian artery.

FIG. 3 is a partial illustration of the abdominal aorta with an aorta stent graft placed in an iliac artery and having a branch vessel prosthesis extending into the hypogastric artery.

FIG. 23 is a partial side view of an introducer for a branch vessel prosthesis.

FIG. 24A-C are cross-sectionals views of the deployment of a branch vessel prosthesis in an aorta stent graft.

FIGS. 27A-H illustrate balloon deployment systems that may used to deploy or expand a branch vessel prosthesis.

DETAILED DESCRIPTION OF THE INVENTION

Figure 1:
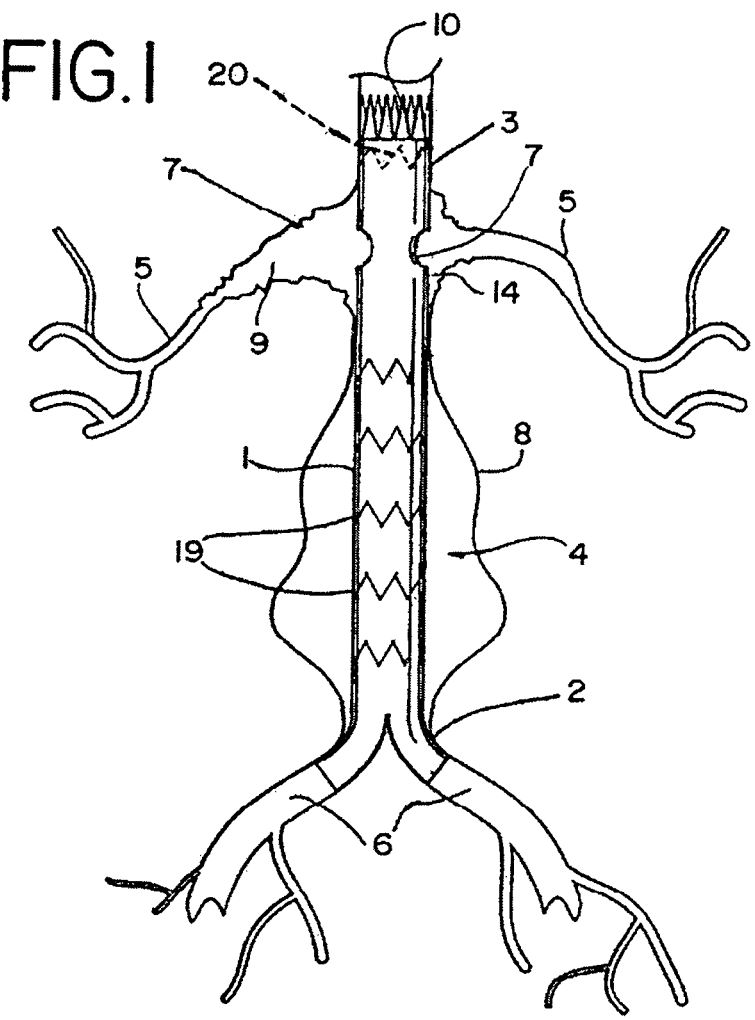
FIG. 1 shows an abdominal aorta with an aorta stent graft having fenestrations aligned with the renal arteries.

To help understand this description, the following definitions are provided with reference to terms used in this application.

Throughout this specification and in the appended claims, when discussing the application of this invention to the aorta or other blood vessels, the term "distal" with respect to such a device is intended to refer to a location that is, or a portion of the device that when implanted is, further downstream with respect to blood flow; the term "distally" means in the direction of blood flow or further downstream. The term "proximal" is intended to refer to a location that is, or a portion of the device that when implanted is, further upstream with respect to blood flow; the term "proximally" means in the direction opposite to the direction of blood flow or further upstream.

The term "prosthesis" means any replacement for a body part or function of that body part. It can also mean a device that enhances or adds functionality to a physiological system. As used herein, "prosthesis" includes a stent, a graft, and/or a stent graft.

The term "endoluminal" describes objects that are found or can be placed inside a lumen in the human or animal body. A lumen can be an existing lumen or a lumen created by surgical intervention. This includes lumens such as blood vessels, parts of the gastrointestinal tract, ducts such as bile ducts, parts of the respiratory system, etc. An "endoluminal prosthesis" is thus a prosthesis that can be placed inside one of these lumens. A stent graft is a type of endoluminal prosthesis.

The term "stent" means any device or structure that adds rigidity, expansion force or support to a prosthesis. In some cases, the stent, by itself, is the prosthesis. A stent may be self-expanding, balloon expandable or may have both characteristics. A zigzag stent is a stent that has alternating struts and peaks (i.e., bends) and defines a generally cylindrical space. A "Gianturco Z stent" is a type of self-expanding zigzag stent. However, variety of other stent configurations are contemplated by use of the term stent.

The term "stent graft" is intended to refer to a prosthesis comprising a stent and a graft material associated therewith that forms a lumen through at least part of its length.

The term "branch vessel" refers to a vessel that branches off from a main vessel. The "branch vessels" of the thoracic and abdominal aorta include the celiac, inferior phrenic, superior mesenteric, lumbar, inferior mesenteric, middle sacral, middle suprarenal, renal, internal spermatic, ovarian (in the female), innominate, left carotid, and left subclavian arteries. As another example, the hypogastric artery is a branch vessel to the common iliac, which is a main vessel in this context. Thus, it should be seen that "branch vessel" and "main vessel" are relative terms.

The term "aorta stent graft" refers to a prosthesis that shunts blood through a main vessel. An "aorta stent graft lumen" runs through the aorta stent graft.

The term flaring, as used herein, encompasses the terms flared and flareable.

An aorta stent graft may be deployed within a body lumen having branch vessels to repair the body lumen. In order to prevent the occlusion of branch vessels, some accommodation may be necessary to preserve flow into those vessels. Thus, for those situations, it is desirable to provide branch vessel prostheses extending from the aorta stent graft into the branch vessels in order to preserve flow to those branch vessels. The present invention provides a branch vessel prosthesis, for use with an aorta stent graft defining a lumen and having a fenestration aligned with a branch vessel, including a flaring portion and a tubular portion. The flaring portion is retained within the lumen of the aorta stent graft and the tubular portion passes through the fenestration and into the branch vessel.

FIG. 1 illustrates a bifurcated aorta stent graft 1 that having a proximal end 2 and a distal end 3, that has been positioned in an abdominal aortic aorta 4 from a point above the renal arteries 5 to a point where the stent graft 1 bifurcates into the iliac arteries 6.

As shown in FIG. 1, the aorta stent graft 1 includes two fenestrations 7 or holes in the stent graft 1 that are aligned with the renal arteries 5, which may accommodate branch vessel prostheses as described further below. In FIG. 1, the aorta 4 has an aneurysm 8 between the renal arteries 5 and the iliac arteries 6 and another aneurysm 9 in the region of the renal arteries 5. The aorta stent graft 1 may include an attachment member 10 for securing the aorta-stent graft 1 to an aortic side wall to prevent migration of the stent graft 1 after it has been placed. The attachment member may comprise a zig zag stent extending from the proximal end 2.

Figure 1A:
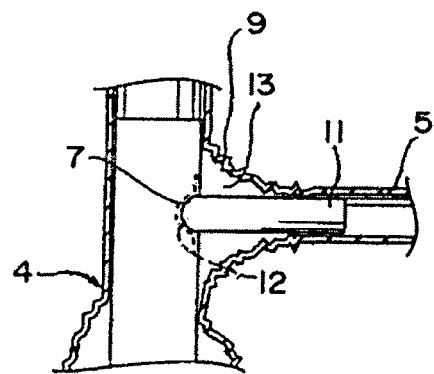
FIG. 1A is a partial side cross-section of the aorta stent graft of FIG. 1 having a branch vessel prosthesis.
Figure 1B:
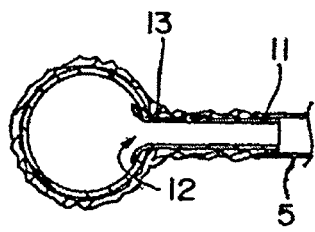
FIG. 1B is a top cross-sectional view of the aorta stent graft of FIG. 1 having a branch vessel prosthesis.

FIG. 1A is a partial side view of the aorta stent graft 1 of FIG. 1 having a branch vessel prosthesis 11 secured within a fenestration 7 of the aorta stent graft 1 and extending into a renal artery 5. FIG. 1B is a top cross-sectional view of the aorta stent graft 1 and the branch vessel prosthesis 11 of FIGS. 1A and 1B. As shown in FIGS. 1A and 1B, a proximal end 12 of the branch vessel prosthesis 11 extends through the fenestration 7 of the aorta stent graft 1 and the aortic ostium 13 into the side branch vessel/renal artery 5, thereby bypassing the aneurysm 9 located in the area of the renal arteries 5.

FIGS. 2A and 3 illustrate aorta stent grafts 1 having fenestrations 7 that are aligned with various vessels that branch off of the aorta 4. For example, FIG. 2A illustrates an aorta stent graft 1 that has been placed within the thoracic aorta 14 that has fenestrations 7 aligned with the left subclavian artery 15 and the left common carotid artery 16. FIG. 2B shows the aorta stent graft 1 of FIG. 2A having a branch vessel prosthesis 11 extending from within the fenestration 7 of the stent graft 1 through to the left subclavian artery 15.

FIG. 3 is a partial illustration of the bifurcated aortic vessel of FIG. 1 at the point of the bifurcation 17 into the iliac arteries 6. As shown, a stent graft 1, having a generally tubular shape, is disposed within the left iliac artery 6' with a fenestration 7 aligned with the hypogastric artery 18. A branch vessel prosthesis 11 extends from the stent graft 1 through the fenestration 7 and into the hypogastric artery 18.

Both the aorta-stent graft 1 and the branch vessel prosthesis 11 may be formed from a biocompatible woven or non-woven fabric or other graft material, and make include one or more external and internal stents, for example, as shown in FIG. 1. For example, along the length of the aorta stent graft 1 and/or the branch vessel prosthesis 11, there may be a number of self-expanding zigzag stents 19 such as Gianturco Z stents on the outside of the body, as shown in FIG. 1. At one or both ends 2, 3 of the aorta stent graft 1 there may be an internal zigzag stent 20 which helps seal against a vascular wall or an interconnecting module. However, the configuration of the stents is not limited to zig zag stents, as any stent configuration known to those in the art can be used.

The outer surface of the tubular body at the ends 2, 3 may present an essentially smooth outer surface that can engage and seal against the wall of the aorta or an adjoining prosthetic module when it is deployed. The internal stent 20 may be comprised of struts with bends at each end of the struts. Barbs may extend from the struts or the bends through the graft material to engage the surrounding vessel wall to prevent distal movement of the aorta stent graft 1 that may be caused by pulsatile blood flow through the aorta stent graft 1. The stents 19, 20 may be joined to the graft material by any known means. Preferably, the stents 19, 20 may be joined to the graft material by stitching, for example by using a monofilament or braided suture material. The branch vessel prosthesis may comprise a stent or series of stents alone or with graft material.

The stents may comprise a balloon-expandable stent or a self-expanding stent. The self expanding stent can include stainless steel, materials with elastic memory properties, such as NITINOL, or any other suitable material. The branch vessel prosthesis 11 may be formed from self-expanding stents such as Z-STENTS®. Z-STENTS® are available from Cook, Incorporated, Bloomington, Ind. USA. The balloon expandable stent portion (typically 316LSS, CoCr, Etc.) can also include a shape memory material having self expanding portion(s) such as titanium, magnesium, nickel, alloys and the like.

Graft material may include a film, a coating, a sheet of biocompatible fabrics, non-woven materials or porous materials. Examples of biocompatible polymers from which porous sheets can be formed include polyesters, such as poly(ethylene terephthalate), polylactide, polyglycolide and copolymers thereof; fluorinated polymers, such as polytetrafluoroethylene (PTFE), expanded PTFE and poly(vinylidene fluoride); polysiloxanes, including polydimethyl siloxane; and polyurethanes, including polyetherurethanes, polyurethane ureas, polyetherurethane ureas, polyurethanes containing carbonate linkages and polyurethanes containing siloxane segments. In addition, materials that are not inherently biocompatible may be subjected to surface modifications in order to render the materials biocompatible. Examples of surface modifications include graft polymerization of biocompatible polymers from the material surface, coating of the surface with a crosslinked biocompatible polymer, chemical modification with biocompatible functional groups, and immobilization of a compatibilizing agent such as heparin or other substances. Thus, any polymer that may be formed into a porous sheet can be used to make a graft material, provided the final porous material is biocompatible. Polymers that can be formed into a porous sheet include polyolefins, polyacrylonitrile, nylons, polyaramids and polysulfones, in addition to polyesters, fluorinated polymers, polysiloxanes and polyurethanes as listed above. Preferably the porous sheet is made of one or more polymers that do not require treatment or modification to be biocompatible.

The graft material may include a biocompatible polyurethane. Examples of biocompatible polyurethanes include THORALON® (Thoratec, Pleasanton, Calif.), BIOSPAN®, BIONATE®, ELASTHANE™, PURSIL™ and CARBOSIL™ (Polymer Technology Group, Berkeley, Calif.). As described in U.S. Patent Application Publication No. 2002/0065552 A1, incorporated herein by reference, THORALON® is a polyetherurethane urea blended with a siloxane-containing surface modifying additive. Specifically, the polymer is a mixture of base polymer BPS-215 and an additive SMA-300.

The graft material may also include extracellular matrix materials. The "extracellular matrix" is typically a collagen-rich substance that is found in between cells in animal tissue and serves as a structural element in tissues. Such an extracellular matrix is preferably a complex mixture of polysaccharides and proteins secreted by cells. The extracellular matrix can be isolated and treated in a variety of ways. Following isolation and treatment, it is referred to as an "extracellular matrix material," or ECMM. ECMMs may be isolated from submucosa (including small intestine submucosa), stomach submucosa, urinary bladder submucosa, tissue mucosa, renal capsule, dura mater, liver basement membrane, pericardium or other tissues.

Purified tela submucosa, a preferred type of ECMM, has been previously described in U.S. Pat. Nos. 6,206,931, 6,358,284 and 6,666,892 as a bio-compatible, non-thrombogenic material that enhances the repair of damaged or diseased host tissues. U.S. Pat. Nos. 6,206,931, 6,358,284 and 6,666,892 are incorporated herein by reference. Purified submucosa extracted from the small intestine ("small intestine submucosa" or "SIS") is a more preferred type of ECMM for use in this invention. Another type of ECMM, isolated from liver basement membrane, is described in U.S. Pat. No. 6,379,710, which is incorporated herein by reference. ECMM may also be isolated from pericardium, as described in U.S. Pat. No. 4,502,159, which is also incorporated herein by reference.

In addition to xenogenic biomaterials, such as SIS, autologous tissue can be harvested as well. Additionally Elastin or Elastin Like Polypetides (ELPs) and the like offer potential as a material to fabricate the covering or frame to form a device with exceptional biocompatibility. Another alternative would be to use allographs such as harvested native valve tissue. Such tissue is commercially available in a cryopreserved state. In addition, a bare metal stent or a covered stent could be coated with an anti-restenotic agent, such as paclitaxel, sirilomis or other equivalent. In addition, the graft can be coated with an anti-thrombogenic agent, such as heparin.

The graft material may be attached to the stent by any means known, for example, the graft material may be attached to the stent by sutures. The graft material also may be affixed to the stent by dipping the stent in a liquefied polymer and allowing the polymer to solidify into a film. The liquefied polymer may be a molten polymer or a polymer or pre-polymer before curing or cross-linking occurs.

Various configurations for the branch vessel prosthesis 11 are illustrated in FIGS. 4-21. The branch vessel prosthesis also may have the structure described in pending U.S. application Ser. No. 10/267,576, filed Oct. 8, 2002, which is hereby incorporated by reference, or U.S. Pat. Nos. 5,718,713, 5,741,327, 5,746,691, 5,843,175, 5,868,782, 6,042,606, 6,299,635 each of which is hereby incorporated by reference.

The branch vessel prosthesis 11 may be a stent, a series of stents, formed from a piece of graft material, or comprise a stent graft. One end of the branch vessel prosthesis 11 is intended to be placed within the lumen of the aorta stent graft 1 through a fenestration 7 in the stent graft 1 as discussed in more detail below and the other end is intended to be placed in a branch vessel. The branch vessel prosthesis 11 is preferably of a size and shape suitable for the branch vessel in which it is to be deployed. Thus, the size and shape of the branch vessel prosthesis 11 may be dictated by the particular anatomy of the patient to be treated and the location where the branch vessel prosthesis 11 is to be place.

The branch vessel prosthesis 11 permits the repair of a diseased or compromised vessel without obstructing blood flow in other portions of the vasculature and conforms to a fenestration 7 of the aorta stent graft 1 without causing swirling in the blood flow and creating the potential for thrombi formation. The branch vessel prosthesis 11 also permits access to all portions of the branch vessel in the event of further interventional treatment. Additionally, the branch vessel prosthesis 11 provides a secure seal between branch vessel prosthesis 11 and a branch vessel, while assisting in anchoring the branch vessel prosthesis 11 to a main vessel, such as an aorta.

Figure 4B:
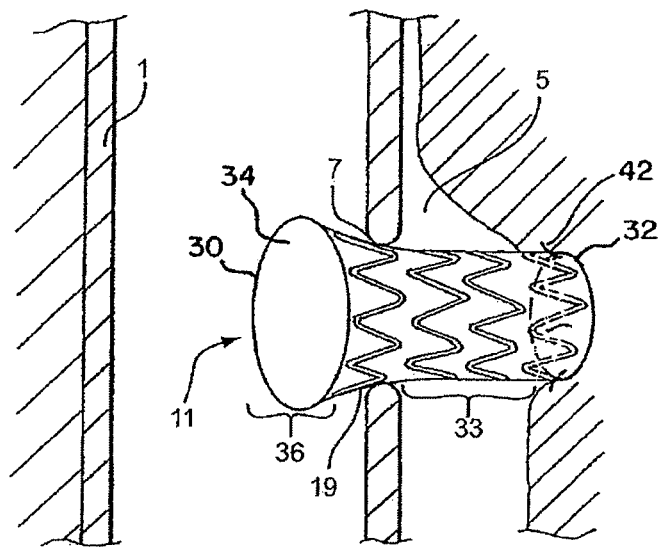
FIG. 4B is a perspective view of the branch vessel prosthesis of FIG. 4A placed in a fenestration of an aorta stent graft.
Figure 4A:
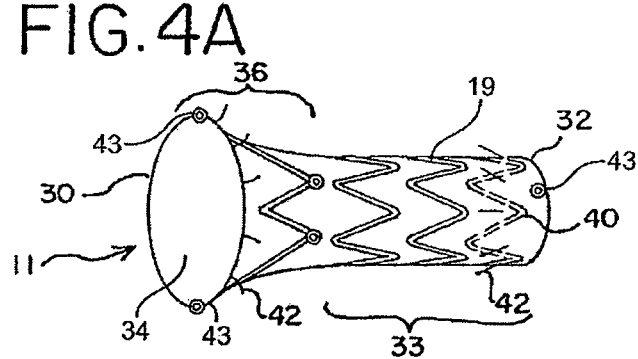
FIG. 4A is a perspective view of a branch vessel prosthesis having a flareable portion and a tubular portion.
Figure 4C:
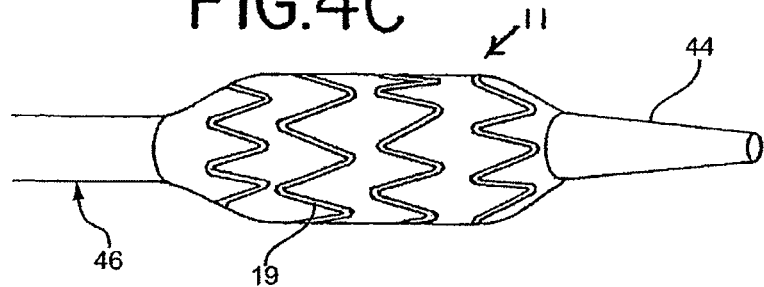
FIG. 4C is perspective view of a partially deployed branch vessel prosthesis.

FIGS. 4A-C generally show a branch vessel prosthesis 11 defining a lumen 34 and having a proximal end 30, a distal end 32, a flaring portion 36, and a tubular portion 33. As described above, the branch vessel prosthesis 11 may comprise graft material and have one or more stents fastened to the inner, the outer, or both surfaces. The distal end 32 may include an internal stent 40 having barbs 42 projecting through the graft material for securement to the branch vessel and to prevent migration of the device after placement. The proximal end 30 or flaring portion 36 may also be provided with attachment mechanism, such as barbs 42, for securing the flaring portion 36 within the aorta stent graft 1.

Preferably, at least a part of the flaring portion 36 has a diameter greater than the diameter of the fenestration 7. Positional indicators 43, such as radiopaque markers, may be attached to or integral with the stent and/or graft material, and may be placed at positions on the branch vessel prosthesis 11 to indicate the proximal end 30, the flaring portion 36 and/or the distal end 32. Preferably, a positional marker 43 is placed so as to indicate that portion of the branch vessel prosthesis 11 that generally aligns with the fenestration 7.

During deployment, the barbs 42 may be enclosed in an endcap 44 of the delivery system 46, as shown in FIG. 4C. As described above, and shown in FIG. 4B, the branch vessel prosthesis 11 is intended to provide a conduit from previously placed aorta stent graft 1 and a branch vessel. The flaring portion 36 extends through the fenestration 7 of the aorta stent graft 1 while the tubular portion 33 extends into the branch vessel.

Figure 5:
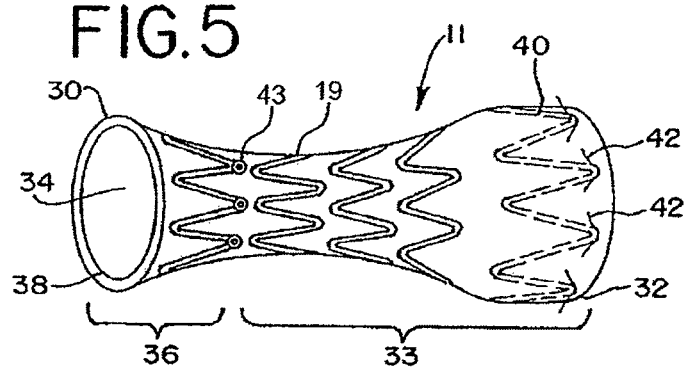
FIG. 5 is perspective view of a branch vessel prosthesis have a reinforcement ring at its proximal end.
Figure 6:
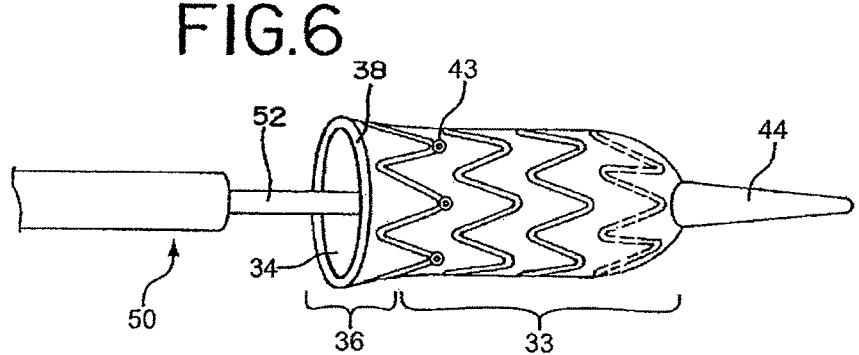
FIG. 6 is a perspective view of the branch vessel prosthesis of FIG. 5 in a partially deployed state.
Figure 7:
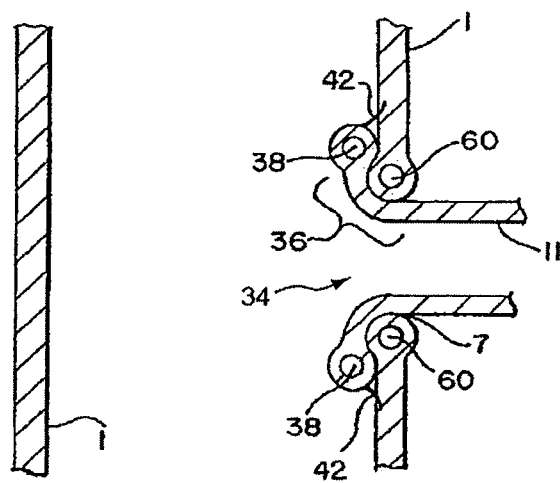
FIG. 7 is a partial cross-sectional view of a branch vessel prosthesis having a reinforcement ring at its proximal end and an aorta stent graft fenestration having a reinforcement ring about its circumference.

FIGS. 5-7 illustrate another embodiment of a branch vessel prosthesis 11. FIG. 5 is a side perspective view of a branch vessel prosthesis 11 in its deployed state. FIG. 6 is a side perspective view of a branch vessel prosthesis 11 in a partially deployed state. FIG. 7 is a partial view in cross-section of an aorta stent graft 1 having a fenestration 7 and a branch vessel prosthesis 11 secured within the aorta stent graft 1 through the fenestration 7. The branch vessel prosthesis illustrated in FIGS. 5-7 includes mating reinforcements 38, 60 for securing the branch vessel prosthesis 11 within the aorta stent graft 1.

As shown in FIG. 5, the branch vessel prosthesis 11 may be a tubular stent graft. The branch vessel prosthesis 11 includes a proximal end 30, a distal end 32, a tubular portion 33, a lumen 34 between the proximal end 30 and the distal end 32, a flaring portion 36, and a reinforcement ring 38 adjacent the proximal end 30. The reinforcement ring 38 may be attached to the flaring portion 36 of the branch vessel prosthesis 11 around its circumference. The reinforcement ring 38 is adapted to engage a second reinforcement ring 60 associated the fenestration 7, as shown in FIG. 7 and discussed in detail with reference to that figure below.

As shown in FIG. 5, the distal end 32 of the branch vessel prosthesis may also be flared to secure the distal end 32 of the branch vessel prosthesis 11 in the branch vessel. The flaring portion 36 and reinforcement ring 38 are deployed within the lumen of an aorta stent graft 1 and retained in the lumen of the stent graft 1. The tubular portion 33 is configured to be received through a fenestration 7. Thus, the remainder of the branch vessel prosthesis 11, the tubular portion 33, is configured to be received and retained within a branch vessel. The distal end 32 may include an internal stent 40 having barbs 42 projecting through the graft material for securement to the branch vessel. One or more external stents 29 may also be secured to the graft material as shown in FIG. 5.

FIG. 6 shows the branch vessel prosthesis 11 of FIG. 5 in a partially deployed state. The branch vessel prosthesis 11 is shown mounted on an introduction system 50 comprising an inner cannula 52 on which the branch vessel prosthesis 11 mounted. The distal end 32 including the barbs 42 enclosed within end cap 44 to permit adjust the placement of the branch vessel prosthesis 11 without causing damage to the vessel wall.

In operation, the introducer system for the branch vessel prosthesis is introduced into the lumen of a previously positioned aorta stent graft. The tubular portion 33 of the branch vessel prosthesis is introduced through the fenestration and into the branch vessel and partially deployed, leaving the barbs enclosed until proper placement is ensured. Thereafter the flaring portion of the branch vessel prosthesis 11 is properly aligned with the fenestration and deployed within the lumen of the aorta stent graft 1. Then the barbed distal end of the tubular portions 33 is released and the prosthesis is placed. If the tubular portion 33 and flaring portion 36 are self expandable, one or more molding balloons may be used to further fit the prosthesis in the aorta stent graft lumen and branch vessel.

Alternatively, the branch vessel prosthesis 11 may comprise balloon expandable stents and may be introduced on a balloon expansion catheter, as described more fully herein. In that case, the flaring portion 36 is flared and the tubular portion 33 is expanded by one or more balloons. In yet another embodiment, the flaring portion 36 is balloon expandable and the tubular portion 33 is self expandable. Other combinations of these types of stents are contemplated as well.

FIG. 7 shows the placement of the proximal end 30 of the branch vessel prosthesis 11 within the lumen 34 of the aorta stent graft 1. The aorta stent graft 1 includes a reinforcement ring 60 positioned around the fenestration 7 wherein the fenestration 7 is substantially aligned with a branch vessel when deployed. As shown in FIG. 7, the flaring portion 36 retains the proximal end 30 of the branch vessel prosthesis 11 within the aorta stent graft 1. The tubular portion 33 extends through the fenestration 7 and into the branch vessel 5 when deployed. Preferably, the branch vessel prosthesis reinforcement ring 60 and the flaring portion 36, have a diameter equal or greater than the diameter of the aorta stent graft reinforcement ring 38.

In a preferred embodiment, both the flaring portion 36 and the branch vessel prosthesis reinforcement ring 38 have a diameter greater than the aorta stent graft reinforcement ring 60. In this embodiment, the branch vessel prosthesis reinforcement ring 38 diameter is greater than the aorta stent graft reinforcement ring diameter so that the flaring portion 36 seals against the fenestration 7 of the aorta stent graft 1 as the branch vessel prosthesis reinforcement ring 38 and the aorta stent graft reinforcement ring 60 engage. Preferably, the branch vessel prosthesis reinforcement ring 38 and the aorta stent graft reinforcement ring 60 at least partially abut.

The aorta stent graft reinforcement ring may be secured to a surface of graft material located on the aorta stent graft. For example, the aorta stent graft reinforcement ring may be secured to an inner surface of the aorta stent graft by sutures, adhesives or other means. The branch vessel prosthesis reinforcement ring also may be secured to a surface of graft material located on the branch vessel prosthesis. The branch vessel prosthesis reinforcement ring may be secured to an outer surface of the flaring portion by the same means.

In one preferred embodiment shown in FIG. 7, both rings 38, 60 may be partially or wholly encased in the graft material. When a penetrable material, such as graft material is used, barbs 42 (as shown in FIG. 7), or other attachment mechanisms may be provided on one or more of the reinforcement rings to further secure the rings. At least one of the rings may be of resilient material to allow compaction until deployment. In addition, at least one of the rings may be made of a shape memory alloy.

The reinforcement rings may be shaped and sized so as to interlock with each other when deployed. In alternate embodiments, the reinforcement rings may comprise hooks or other mechanical fastening means. For example, one of the reinforcement rings can include a surface with loops and the other of the reinforcement rings can include a surface with hooks, such as in the material known as Velcro®, so as to facilitate attachment of the two reinforcement rings to each other when deployed. In another example, one of the reinforcement rings can include tabs and the other reinforcement ring can include holes for receiving the tabs to facilitate attachment of the two reinforcement rings to each other when deployed. In another embodiment, at least one of the reinforcement rings comprises a magnetic material so that the reinforcement rings are drawn together by magnetic force when deployed.

At least one of the reinforcement rings can include a surface of a sealing material to facilitate a seal between the aorta stent graft and the branch vessel prosthesis. In addition, both of the reinforcement rings can comprise a surface of a sealing material to facilitate a seal between the aorta stent graft and the branch vessel prosthesis. For example, one of the reinforcement rings can include a surface with a biocompatible adhesive to facilitate attachment of the two reinforcement rings to each other when deployed.

As with the branch vessel prosthesis 11 described in FIGS. 4A-C, positional indicators may be located at any point on the branch vessel prosthesis 11. In particular, positional indicators 43, such as radiopaque or other types of markers that would be visible to the doctor during deployment, may be located at the proximal end 30, the distal end 32 and the point of the graft intended to align with the fenestration of the aorta stent graft 1.

The branch vessel prosthesis 11 of FIGS. 5-6 is deployed, for example, by introducing the prosthesis 11 into an aorta stent graft 1 such that the flaring portion 36 retains the proximal end of the branch vessel prosthesis in the aorta stent graft, the tubular portion extends through the fenestration 7 and into the branch vessel 5, and the reinforcement rings 38, 60 engage one another.

Figure 8:
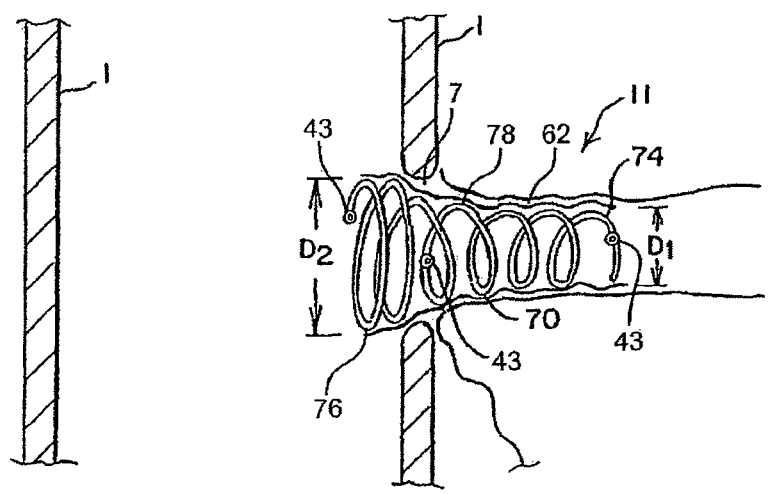
FIG. 8 and FIG. 28 illustrates a branch vessel prosthesis comprising a helical coil stent graft positioned in an aorta stent graft and the branch vessel.
Figure 9:
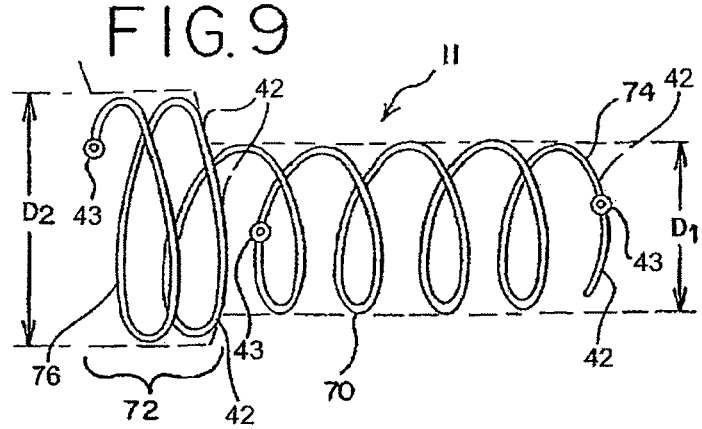
FIG. 9 shows the helical coil branch vessel prosthesis of FIG. 8 and FIG. 28 in greater detail.
Figure 10:
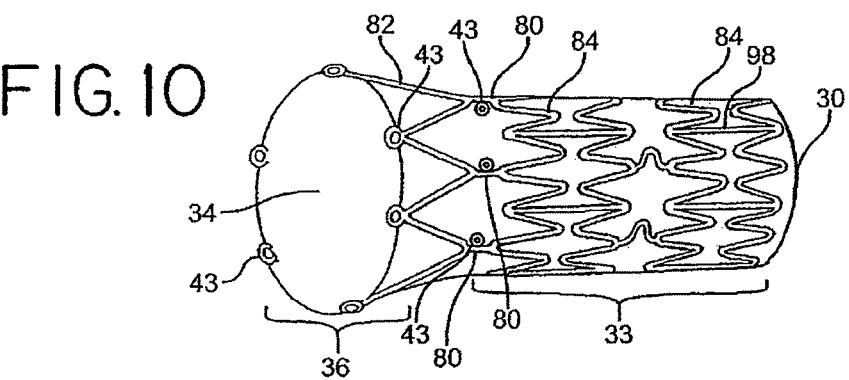
FIG. 10 shows a branch vessel prosthesis having a flareble stent portion.

Another branch vessel prosthesis 11 is shown in FIGS. 8 and 9. The branch vessel prosthesis 11 includes a generally helical coiled stent 70. Graft material 62 may be affixed thereto to form a branch vessel lumen 34. For example, when the aneurysm extends into the branch vessel, the helical coil stent is preferably covered with graft material. However, if the aneurysm stops short of the branch vessel, a bare helical coil stent may be used to maintain patency of the branch vessel and/or to maintain alignment of the aorta stent graft with the fenestration.

The graft material 62 may be attached to the helical coil stent 70 by any means known, for example, the graft material may be attached to the helical coil stent 70 by sutures. The graft material 62 may be any of the materials described previously for use as graft materials. For example, the graft material may be a woven fabric or a polymer film. The graft material also may be affixed to the helical coil stent 70 by dipping the stent in a liquefied polymer and allowing the polymer to solidify into a film. The helical coil may be composed of a metal wire.

The helical coiled stent 70 may be an expandable stent including a flaring portion 72 that is deployed within the aorta stent graft 1, and a distal portion 74 that is deployed within the branch vessel 5, such as a renal artery. The proximal end of the branch vessel prosthesis 11 may form a seal with an inner surface of the aorta stent graft 1 around the fenestration 7. The fenestration 7 may include a reinforcement around the fenestration 7. For example, the reinforcement may be a reinforcement ring 60, such as that shown and described previously with reference to FIG. 7. In this example, the reinforcement ring cooperates with at least one full turn of the helical coil stent 70 at the proximal end 76 to form a seal between the aorta stent graft and the branch vessel stent graft.

Figure 28:
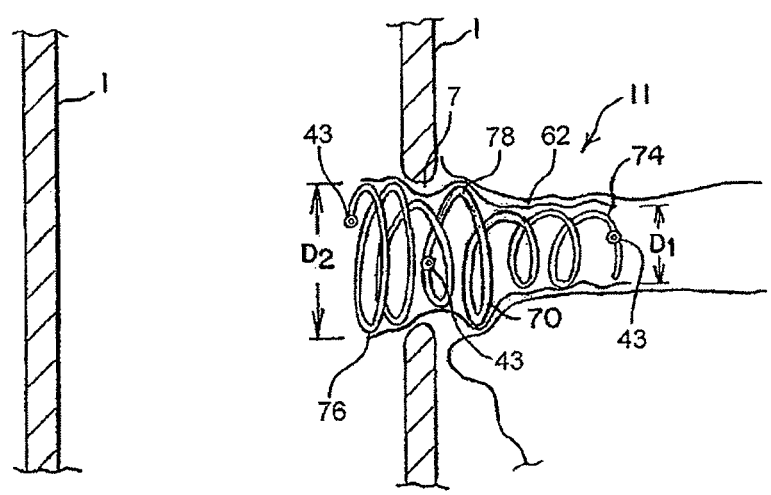

As shown in FIG. 8 and FIG. 28, the flaring portion 72 has a larger diameter D2 than the distal portion diameter D1 and may assist to pull the aorta stent graft 1 and the branch vessel 5 together. The diameter of the turn of the coil 78 immediately adjacent an outer surface of the fenestration 7 may also be greater than the diameter of the fenestration 7 to thereby capture the fenestration 7 between two adjacent coils. Preferably, the diameter of the turn of the coil 78 is only slightly greater than the diameter of the fenestration. In one embodiment, one full turn of the helical coil stent at a proximal end has a diameter larger than the diameter of the fenestration, and at least two full turns of the helical coiled stent have a diameter smaller than the diameter of the fenestration.

During deployment, at least two full turns of the helical coil are passed through the fenestration into the branch vessel while the proximal end with at least one full turn is retained in the aorta stent graft 1 lumen. Positional indicators 43 may be located on the proximal and distal most coils, as well as at the location of the coil where the coiled stent flares, so as to indicate the position of alignment with the fenestration. The coil may also be provided with barbs 42 or some other fastening mechanism, either on the coil itself or attached to graft material to facilitate attachment of the device to the branch vessel wall and/or the lumen of the aorta stent graft.

Another branch vessel prosthesis configuration is shown in FIGS. 10-14. The branch vessel prosthesis 11 includes a stent having a flaring proximal portion 36, a tubular section 33, a bending portion 80 at a junction between the flareable proximal portion 36 and the tubular portion 33 and a distal end 30, for use with an aorta stent graft 1 defining a lumen and having a fenestration aligned with a branch vessel. The branch vessel prosthesis 11 preferably includes an expandable stent with a graft material affixed thereto to form a branch vessel lumen. The tubular portion 33 of the branch vessel prosthesis 11 may comprise a self expanding stent while the flaring portion 36 may be a balloon expandable stent. Alternatively, both portions may be balloon expandable.

In one preferred embodiment, the proximal stent 82 is connected to the proximal body stent 86 by the bending portion 80. In another embodiment, when the stent is encapsulated in graft material such as Thoralon, the proximal stent 82 may not be directly connected to the proximal body stent 86 and the Thoralon material between the proximal stent 82 and the proximal body stent 86 may form the bending portion 80.

In the embodiment of FIGS. 10-14, the branch vessel prosthesis 11 is deployed such that the bending portion 80 is aligned with a fenestration 7 of the aorta stent graft 1, the flaring portion 36 resides within the lumen of the aorta stent graft 1 and the tubular portion 33 resides in the branch vessel. Upon deployment, the flaring of the flaring portion 36 is preferably accomplished by a balloon that facilitates bending of the bending portion 80.

As shown in FIGS. 10-14, the branch vessel prosthesis 11 may comprise a multi-cell stent structure having a proximal cell 82 intended to be the cell closest to the ostium or branch vessel entrance. The proximal cell 82 is connected to a plurality 83 of interconnected body cells 84. Each cell is a substantially circular ring comprising an endless undulating pattern.

Figures 11, 12:
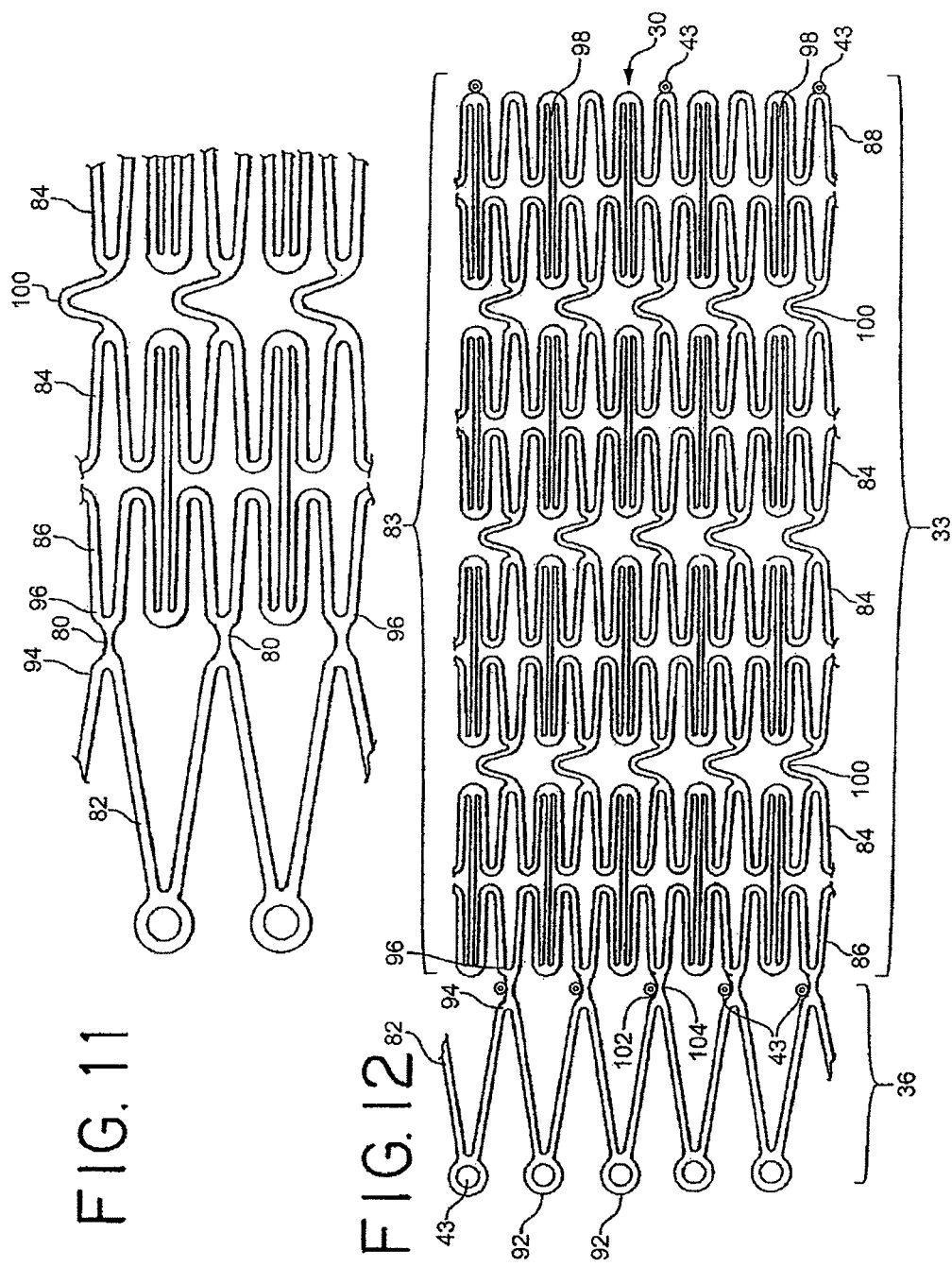
FIGS. 11-14 are partial views of a stent configuration having a bending portion for use with a branch vessel prosthesis.
Figure 13:
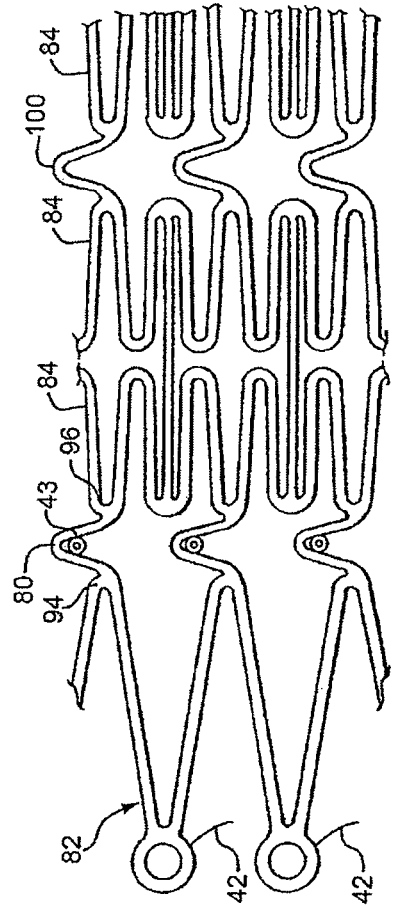
Figure 14:
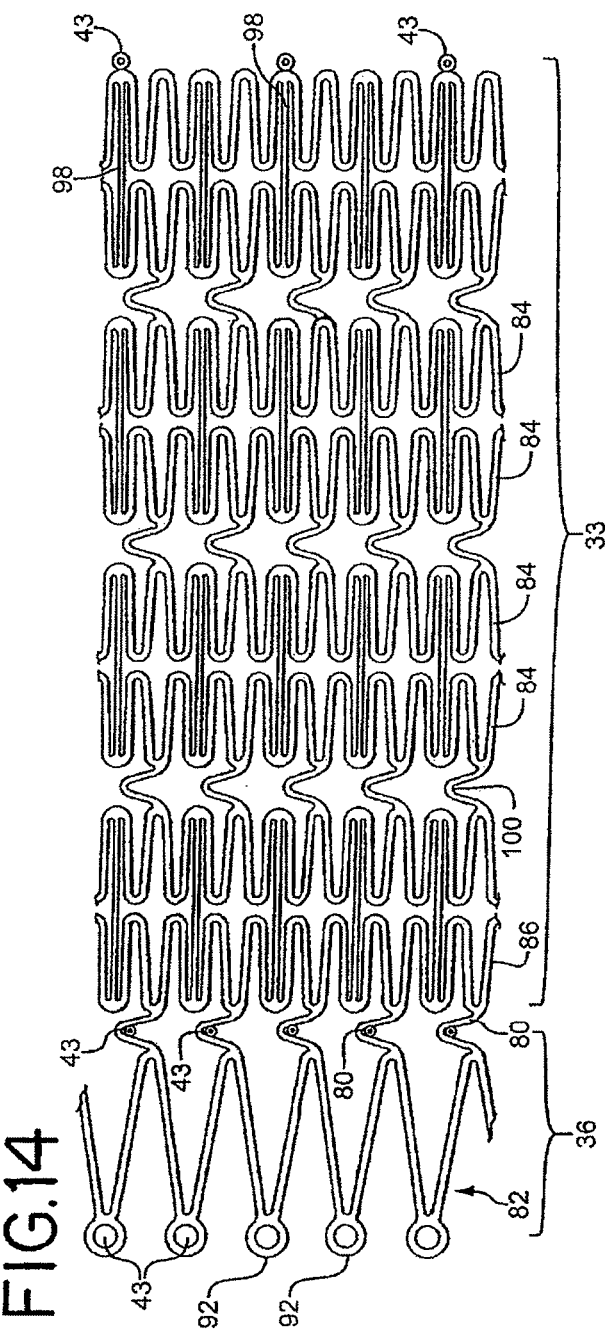
Figure 15:
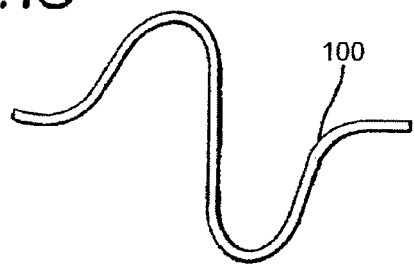
FIGS. 15-16 are partial views of alternative bending portions.
Figure 16:
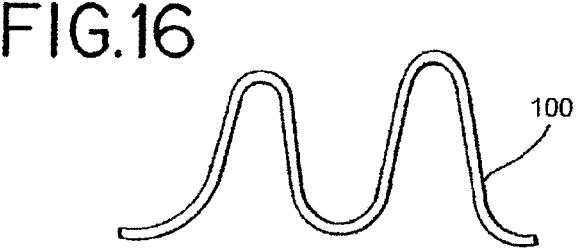

As shown in FIGS. 12-14, the plurality 83 of interconnected body cells 84 forms the tubular portion 33 of the branch vessel prosthesis 11 and includes a proximal body-cell 86 and a distal body cell 88. When deployed, the proximal body cell 86 is the body cell closest to the fenestration 7 (and thus the ostium of the main vessel) and is connected to the proximal cell 82. The distal body 88 cell is the body cell farthest from the fenestration 7 (and thus the ostium of the main vessel).

The proximal cell 82 is configured to flare-out in the expanded configuration and forms the flaring portion 36 of the branch vessel prosthesis 11. The proximal cell configuration is contemplated to form the flaring portion 36. For example, the proximal cell 82 may be configured with a wider cell width or a longer strut length than the body cells 84. As shown in the Figures the peaks 92 of the proximal cell 82 are unattached and free to separate and thereby permit the flaring portion 36 to flare-out in the expanded configuration. It should be noted that, as used herein the term "peak" is interchangeable with the term "valley" and both refer to a turn or bend in a stent cell.

Also, the frequency of the points of attachment between the flaring portion 36 and the tubular portion 33 can be varied to facilitate bending in the bending portion 80 of the branch vessel prosthesis 11 in the expanded configuration. As shown in the 11-13, each peak 94 along the distal edge of the proximal cell 82 is connected to every other peak 96 along the proximal edge of the proximal body cell 86. The flaring of the flaring portion 80 in the expanded configuration may be decreased if each peak along the distal edge of the proximal cell is connected to each peak along the proximal edge of the proximal body cell. Conversely, interconnecting each proximal cell peak to every third proximal body cell peak increases the ability of the flaring portion to flare in the expanded configuration.

Each of the plurality of interconnected body cells 84 may have a shorter cell width and shorter strut length than the proximal cell 82. Further, adjacent body cells 84 are connected to each other by tie-bars 98 and/or connection members 100. Flexibility along the body cells may be provided by altering the shape of the connection members 100. Thus, the connection member may comprise a "V" shape (FIGS. 10-14), an "S" shape (FIG. 15) or a "W" shape (FIG. 16) to increase the flexibility of the tubular portion 36 of the branch vessel prosthesis 11.

The bending portion 80 interconnects the proximal cell 82 to the plurality of interconnected body cells 84. The bending portion 80 also forms a junction between the flaring portion 36 and the tubular portion 33 of the branch vessel prosthesis 11. The bending portion 80 minimizes the stress imposed by the flaring portion 36 on the tubular portion 33 in the expanded configuration by providing a point of flexibility.

Increasing the flexibility of bending portion 80, increases the ability of the flaring portion 36 to flare-out in the expanded configuration. Flaring of the flaring portion 36 is thus facilitated by the bending portion 80.

Multiple configurations of the bending portion 80 are contemplated. In one embodiment, such as that depicted in FIGS. 10 and 11, the bending portion 80 includes metal struts having a reduced diameter to facilitate bending at the bending portion 80. For example, the bending portion 80 may undergo some form of material reduction to enhance the flexibility between the proximal cell 86 and the plurality 83 of body cells 84. Thus, as shown in FIG. 12, the side edges 102, 104 of the bending portion 80 may comprise a radius of curvature such that the bending portion 80 forms an hour-glass configuration. Increasing the radius of curvature along the edges of the bending portion 80 increases the flexibility of the bending portion 80. Similarly, the top and bottom surfaces of the bending portion 80 may be polished to enhance flexibility.

In other embodiments, the metal struts can be heat treated or mechanically worked to facilitate bending at the bending portion.

In still other embodiments, the configuration of the bending portion 80 may be altered to enhance the flexibility. Thus, the bending portion 80 may comprise a "V" shape (FIG. 11), an "S" shape (FIG. 15), a "W" shape (FIG. 16) to increase the flexibility between the flaring portion 36 and tubular portion 33 of the branch vessel prosthesis 11.

In still yet other embodiments, the material at the bending portion 80 may be more bendable than the material of the tubular portion or flaring portion.

In still yet another embodiment, the bending portion 80 may include fewer struts per unit area than the tubular portion 33 or the flaring portion 36 to thereby facilitate bending at the bending portion 80.

Figure 17:
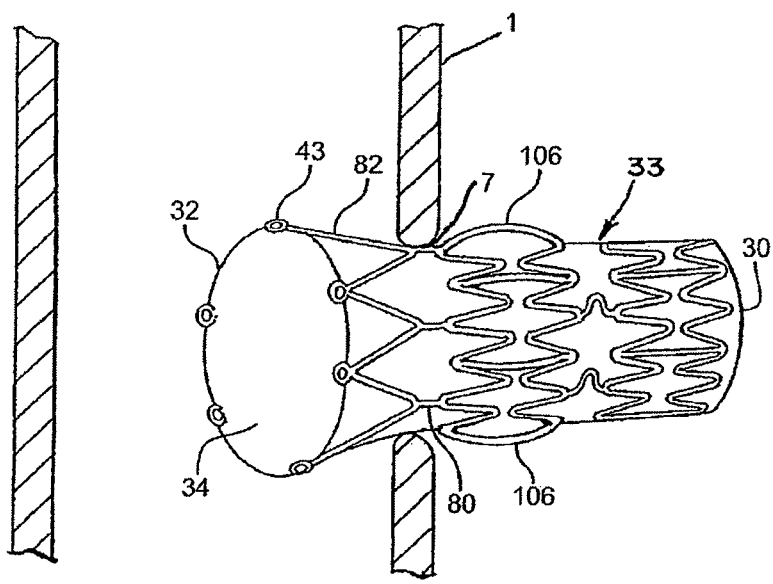
FIG. 17 shows a branch vessel prosthesis in which a portion of the stent forms a proximal bulge.

In the alternate embodiment shown in FIG. 17, using the principles described above, the proximal body cell 86 may be configured to expand or "bulge" 106 to secure the branch vessel prosthesis 11 against the main vessel 4.

As with previous embodiments, positional indicators 43 may be associated with the branch vessel prosthesis to facilitate visualization of the prosthesis during and after deployment. For example, positional indicators 43 may be on or associated with the proximal cell 82 and the distal end 30. Preferably, at least one positional indicator is positioned on or associated with the bending portion 80 of the branch vessel prosthesis 11 to facilitate alignment of the bending portion with the fenestration 7 of the aorta stent graft 1. As shown in FIGS. 10-14, for example, positional indicators 43 may be located at or associated with the apices of the proximal cell 82, located at or associated with the bending portion 80, and located at or associated with the distal end 86.

The branch vessel prosthesis 11 of this embodiment may also be provided with barbs or other fastening mechanisms, either on the stent itself or attached to graft material to facilitate attachment of the device to the branch vessel wall and/or the lumen of the aorta stent graft 1. For example, the proximal cell 82 may be provided with barbs 42, as shown in FIG. 13.

Figure 18:
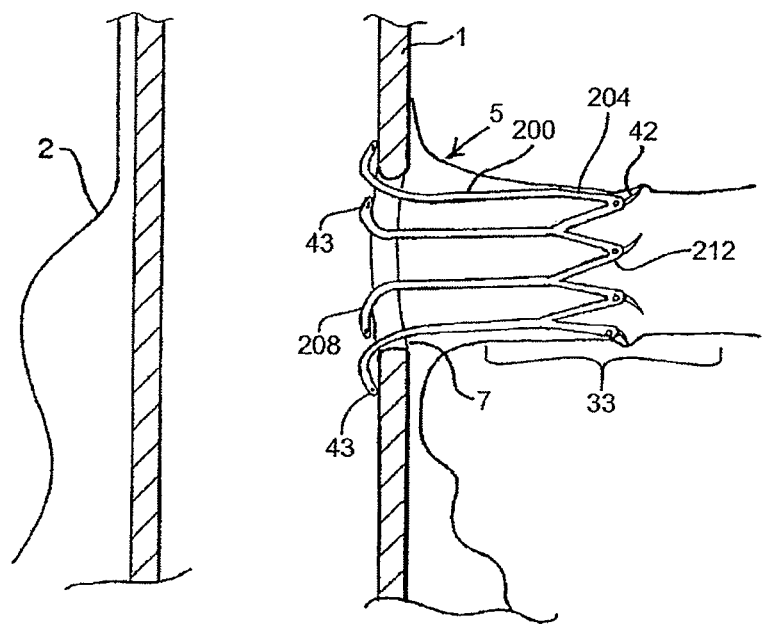
FIG. 18 is a partial cross-sectional view of a branch vessel prosthesis positioned in an aorta stent graft having a flaring attachment mechanism.
Figure 19:
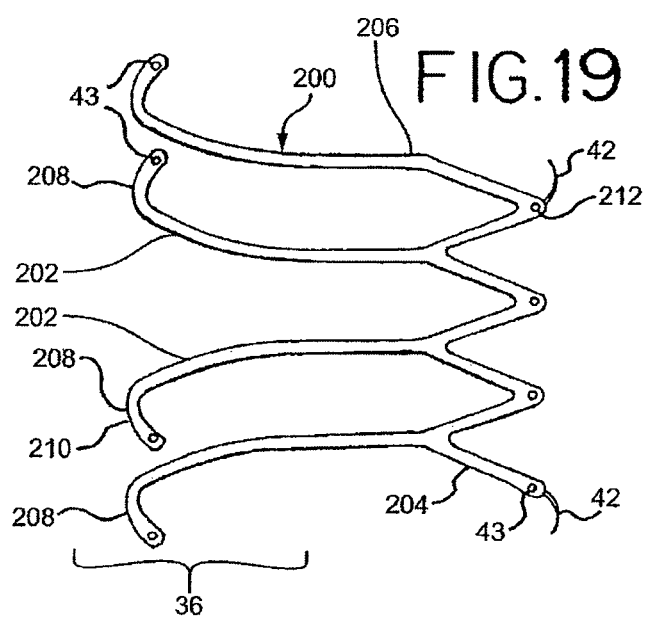
FIG. 19 shows the attachment mechanism of FIG. 18.

Another branch vessel prosthesis configuration is shown in FIGS. 18 and 19. As shown, the branch vessel prosthesis 11 has a flaring portion 36 and a tubular portion 33 with an anchoring device 200, such that when deployed, the flaring portion 36 is located within the lumen of the aorta stent graft 1 and the tubular portion 33 passes through the fenestration 7 and into the branch vessel 5, with the anchoring device 200 affixing the position of the tubular portion 202 within the branch vessel 5. Upon deployment, the system further allows the tubular portion 33 to be inserted and affixed a predetermined depth into the branch vessel 5 such that the flaring portion 36 is maintained against an inside wall of the aorta stent graft 1 to thereby bias the aorta stent graft 1 toward the branch vessel 5.

The flaring portion 36 is configured to engage a fenestration 7 of the aorta stent graft 1. The anchoring device 200 comprises securement arms 202. That extend within the fenestration 7 of the aorta stent graft 1 and secure the branch vessel stent graft 11 against the fenestration 7 of the aorta stent graft 1 and the ostium of the branch vessel 5. In this example, the branch vessel prosthesis 11 includes metal struts in the flaring portion 36 that form an acute angle with the tubular portion 33 such that when the tubular portion 36 is inserted a predetermined depth into the branch vessel 5, the flaring portion 36 is maintained against an inside wall of the aorta stent graft 1 to thereby bias the aorta stent graft 1 toward the branch vessel 5. When deployed, the metal struts are curved through than arc of more than 90 degrees with respect to the tubular portion 33. For example, when deployed, the metal struts may be curved through an arc of about 180 degrees with respect to the tubular portion.

As shown in FIGS. 18-19, the anchoring device 200 may comprise a zig zag portion 204 with the securement arms 202 extending from the proximal apices 206 of the zig zag portion 204. The proximal ends 208 of the securement arms 202 may form an arc or hook 210 at the ends 208 of the arms 202 for anchoring the flaring portion 36 of the branch vessel prosthesis 11 with the aorta stent graft 1. Anchoring barbs 42 may provided at the distal apices 214 of the zig zag portion 204. Positional indicators 43 Radiopaque or other visual markers 43 may also be provided at the distal apices 212, the proximal ends 208 of the arms 208 to facilitate viewing of the branch vessel prosthesis 11 during and after deployment.

Figure 20:
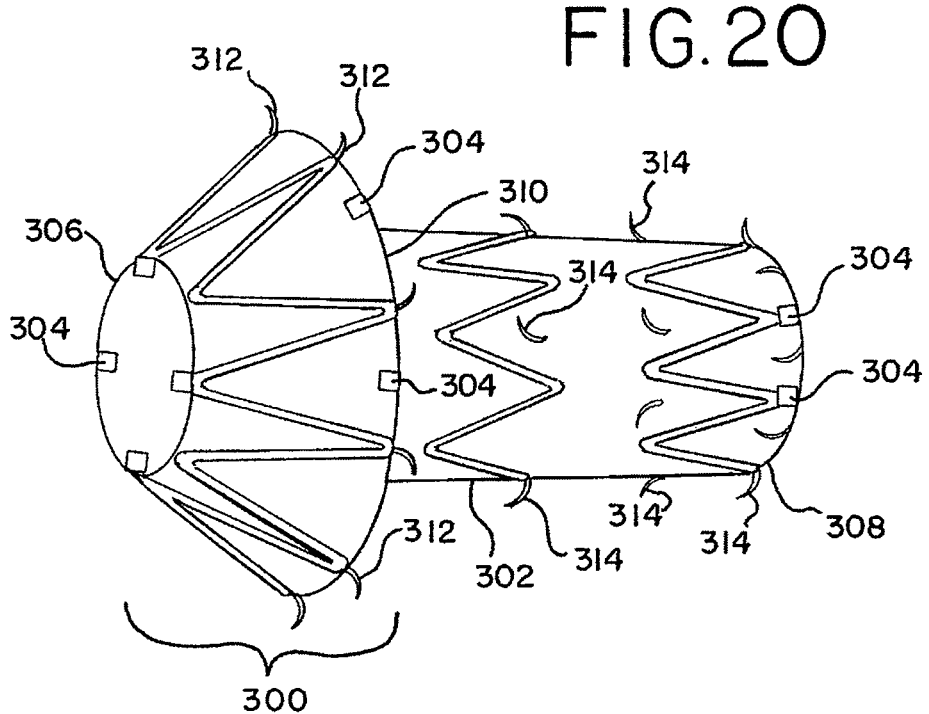
FIG. 20 is a perspective view of branch vessel prosthesis having an inverted flaring portion.
Figure 21:
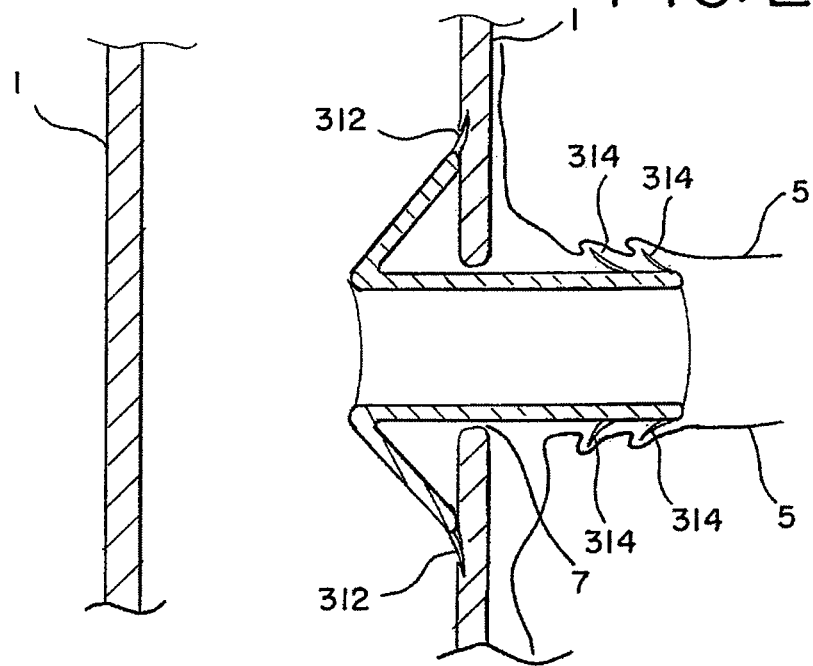
FIG. 21 is a cross-sectional view of the branch vessel prosthesis of FIG. 20 placed in an aorta stent graft and branch vessel.

Another branch vessel configuration is shown in FIGS. 20-21. In this configuration the flaring portion 300 that is configured to engage a fenestration 7 of the aorta stent graft 1 is inverted relative to the flaring portions of other configurations shown here. In other words, in this configuration, as shown in FIG. 21, the flaring portion 300 forms an acute angle with respect to the tubular portion 302, and forms a seal with an inner surface of the lumen of the aorta stent graft 1. As shown in FIG. 21, the flaring portion 300 extends through the fenestration 7 of the aorta stent graft 1 and secures the branch vessel prosthesis 11 against the aorta stent graft 1.

In this configuration, positional indicators 304 may be located at or associated with the proximal end 306, the distal end 308 and/or the rim 310 of the flaring portion 300. Additionally, one or more fastening barbs 312 may be placed circumferentially about the rim the rim 310 of the flaring portion 300 to secure the rim 310 to the aorta stent graft 1 as shown in Figures. Additional barbs 314, may be included on the tubular portion 316 of the branch vessel prosthesis 11 to secure the tubular portion 316 to the branch vessel 5. As shown in the Figures, the additional barbs 314 may be circumferentially placed about the tubular portion 316 in one or more sets of the additional barbs 314.

The Introducer

Figure 22:
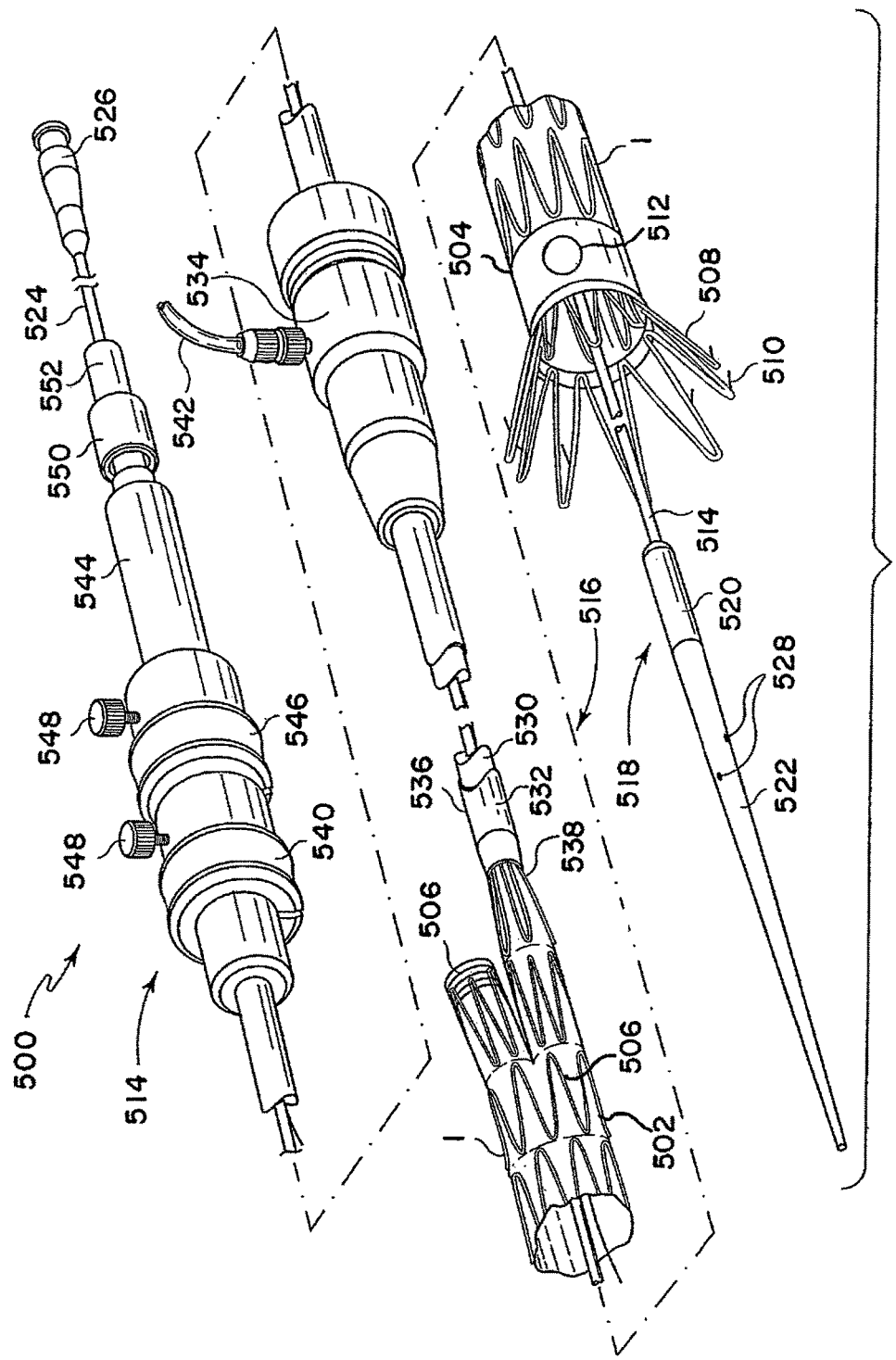
FIG. 22 is an exploded perspective view of an introducer system that may be used to deploy an aorta stent graft or a branch vessel prosthesis.

FIG. 22 shows a self-expanding aorta stent graft 1, and an endovascular deployment system 500, also known is an introducer 100, that may be used to deploy the aorta stent graft 1 in a main vessel, such as the abdominal or thoracic aorta, of a patient during a medical procedure. These items are each described in greater detail in PCT application WO 98/53761. The same deployment system 500 may be used for the deployment the branch vessel prosthesis and, thus, FIG. 22 is fully applicable thereto.

The aorta stent graft 1 has an expandable tubular portion 502 having a proximal end 504, and a distal end 506. The aorta stent graft 1 comprises a tubular graft material, such as woven polyester, with self-expanding stents 506 attached thereto. The self-expanding stents 506 cause the aorta stent graft 1 to expand following its release from the introducer 500. The aorta stent graft 1 also includes a self-expanding proximal stent 508 that extends from its proximal end 504. The proximal stent 508 may have distally extending barbs 510. When it is released from the introducer 500, the proximal stent 508 anchors the barbs 510, and thus the proximal end 504 of the aorta stent graft 1, to the lumen of the patient. The proximal end 504 of the aorta stent graft 1 is provided with one or more fenestrations 512 that are intended to align with a branch vessel.

The introducer 500 includes an external manipulation section 514, a distal attachment region 516 and a proximal attachment region 518. The distal attachment region 516 and the proximal attachment region 518 secure the distal and proximal ends of the aorta stent graft 1, respectively. During the medical procedure to deploy the aorta stent graft 1, the distal and proximal attachment regions 516 and 518 will travel through the lumen to a desired deployment site. The external manipulation section 514, which is acted upon by a user to manipulate the introducer, remains outside of the patient throughout the procedure.

The proximal attachment region 518 of the introducer 500 includes a cylindrical sleeve 520. The cylindrical sleeve 520 has a long tapered flexible extension 522 extending from its proximal end. The flexible extension 522 may be substantially aligned with a longitudinal axis of the introducer 500, as shown in FIG. 22. Alternatively, flexible extension 522 may curve to accommodate curves or turns in a patient's anatomy, as shown in FIGS. 23 and 24A-B. The flexible extension 520 has an internal longitudinal aperture (not shown). This longitudinal aperture facilitates advancement of the tapered flexible extension 522 along an insertion wire (not shown). The longitudinal aperture also provides a channel for the introduction of medical reagents. For example, it may be desirable to supply a contrast agent to allow angiography to be performed during placement and deployment phases of the medical procedure.

A thin walled metal tube 524 is fastened to the extension 522. The thin walled metal tube 524 is flexible so that the introducer 500 can be advanced along a relatively tortuous vessel, such as a femoral artery, and so that the distal attachment region 516 can be longitudinally and rotationally manipulated. The thin walled metal tube 524 extends through the introducer 500 to the manipulation section 514, terminating at a connection means 526.

The connection means 526 is adapted to accept a syringe to facilitate the introduction of reagents into the thin walled metal tube 524. The thin walled metal tube 524 may be in fluid communication with the apertures 528 of the flexible extension 522. Therefore, reagents introduced into connection means 526 will flow to and emanate from the apertures 528.

A plastic tube 530 is coaxial with and radially outside of the thin walled metal tube 524. The plastic tube 530 is "thick walled"—its wall is preferably several times thicker than that of the thin walled metal tube 524. A sheath 532 is coaxial with and radially outside of the plastic tube 530. The thick walled plastic tube 530 and the sheath 532 extend distally to the manipulation region 514.

During the placement phase of the medical procedure, the aorta stent graft 1 is retained in a compressed condition by the sheath 532. The sheath 532 extends distally to a gripping and hemostatic sealing means 534 of the external manipulation section 526. During assembly of the introducer 500, the sheath 532 is advanced over the cylindrical sleeve 520 of the proximal attachment region 518 while the aorta stent graft 1 is held in a compressed state by an external force. A distal attachment (retention) section 536 is coupled to the thick walled plastic tube 530. The distal attachment section 536 retains a distal end 538 of the aorta stent graft 1 during the procedure. Likewise, the cylindrical sleeve 520 retains the proximal stent 508.

The distal end 538 of the aorta stent graft 1 is retained by the distal attachment section 536. The distal end 538 of the aorta stent graft 1 has a loop (not shown) through which a distal trigger wire (not shown) extends. The distal trigger wire extends through an aperture (not shown) in the distal attachment section 536 into an annular region between the thin walled tube 524 and the thick walled tube 530. The distal trigger wire extends through the annular space to the manipulation region 514. The distal trigger wire exits the annular space at a distal wire release mechanism 540.

The external manipulation section 514 includes a hemostatic sealing means 534. The hemostatic sealing means 534 includes a hemostatic seal (not shown) and a side tube 542. The hemostatic sealing means 534 also includes a clamping collar (not shown) that clamps the sheath 532 to the hemostatic seal, and a silicone seal ring (not shown) that forms a hemostatic seal around the thick walled plastic tube 530. The side tube 542 facilitates the introduction of medical reagents between the thick walled tube 530 and the sheath 532.

A proximal portion of the external manipulation section 514 includes a release wire actuation section that has a body 544. The body 544 is mounted onto the thick walled plastic tube 530. The thin walled tube 524 passes through the body 544. The distal wire release mechanism 540 and the proximal wire release mechanism 546 are mounted for slidable movement onto the body 544.

The positioning of the proximal and distal wire release mechanisms 540 and 544 is such that the proximal wire release mechanism 540 must be moved before the distal wire release mechanism 544 can be moved. Therefore, the distal end 538 of the aorta stent graft 1 cannot be released until the proximal stent 508 has been released, and the barbs 510 have been anchored to the lumen. Clamping screws 548 prevent inadvertent early release of the aorta stent graft 1. A hemostatic seal (not shown) is included so that the release wires can extend out through the body 544 without unnecessary blood loss during the medical procedure.

A distal portion of the external manipulation section 514 includes a pin vise 550. The pin vise 550 is mounted onto the distal end of the body 544. The pin vise 550 has a screw cap 552. When screwed in, vise jaws (not shown) of the pin vise 550 clamp against or engage the thin walled metal tube 524. When the vise jaws are engaged, the thin walled tube 524 can only move with the body 544, and hence the thin walled tube 524 can only move with the thick walled tube 530. With the screw cap 552 tightened, the entire assembly can be moved together as one piece.

A second introducer based on the same principles as the introducer 500 described above may also be adapted so that it can introduce a self-expanding branch vessel prosthesis by passing it through the fenestration 512 in the aorta stent graft 562. As shown in FIGS. 23 and 24A-C the introducer 500, having a curved flexible extension 522, may be introduced into the lumen 560 of a previously placed stent graft 562, and through the fenestration 564 into the branch vessel 566. Once positioned properly, the sheath 532 may be retracted, and the branch vessel prosthesis 568 expanded. Any barbs 570 located at the distal end 572 of the branch vessel prosthesis 568, remain in the end cap 574 until the prosthesis is properly placed. The end cap 574 is released during deployment by a trigger wire. Deployment of the branch vessel prosthesis is discussed in further detail below.

Figure 25:
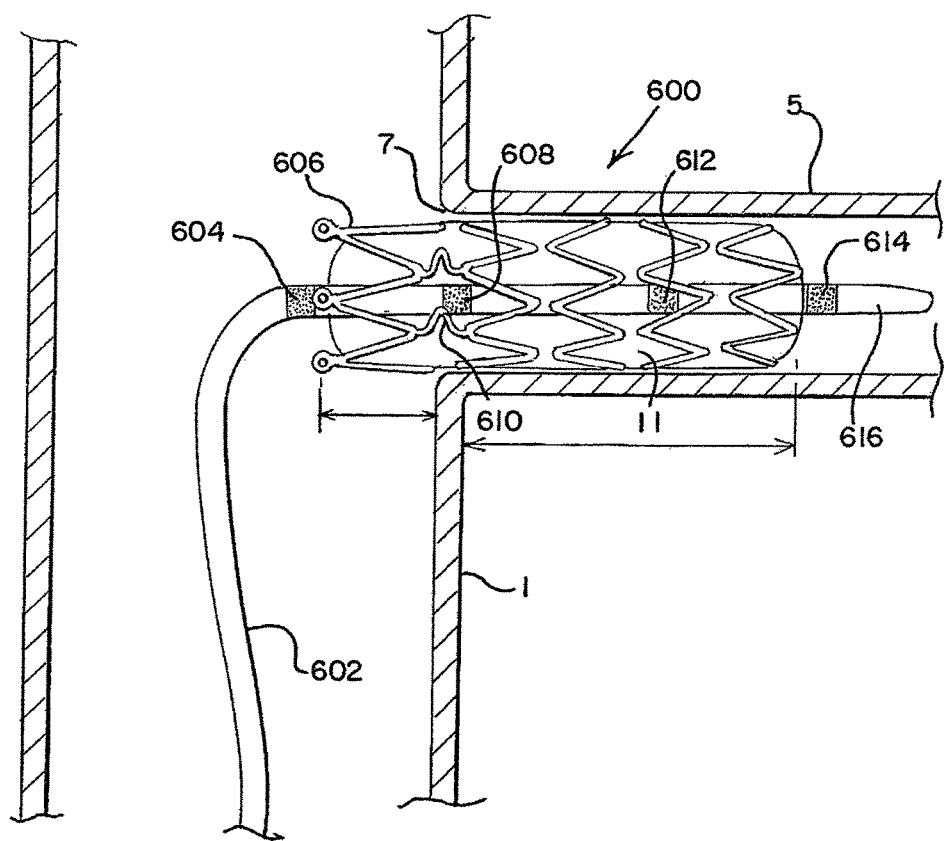
FIG. 25 is a cross-sectional view of a positional indicator system for use with a branch vessel prosthesis.

As shown in FIG. 25, the introducer for the branch vessel prosthesis 11 may include a positional indicator system 600, either to compliment or to replace the positions indicator system on the branch vessel prosthesis. As discussed above, positional indicators may be placed on or associated with the branch vessel prosthesis 11 indicate various points on the branch vessel prosthesis 11. Also, as previously discussed, one or more positional indicators may be placed on or associated with the fenestration 7 of the aorta stent graft 1. The system shown in FIG. 25 includes multiple positional indicators on the introducer 602. A first positional indicator 604 is positioned on the introducer 602 and indicates the position of the proximal end 606 of the branch vessel prosthesis 11. A second positional indicator 608 is positioned on the introducer 602 and indicates the position of that part of the branch vessel prosthesis 11 that is to be aligned with the fenestration 7 of the aorta stent graft 1.

In FIG. 25, the second positional indicator 608 indicates the bending portion 610 of the branch vessel prosthesis 11. A third positional marker 612 is located on the introducer 602 and indicates the position of branch vessel prosthesis 11 tubular portion. A fourth positional indicator 614 may be positioned on or near the end cap 616 to indicate the distal end of the branch vessel prosthesis 11. Other positional indicators may be included on the introducer at other locations as may be desired to facilitate visualization of the branch vessel prosthesis 11 branch vessel prosthesis during and after deployment. These positional indicators may be used alone or in combination with positional indicators on the branch vessel prosthesis 11 and/or the aorta stent graft 1 to further enhance visualization.

Figure 26A:
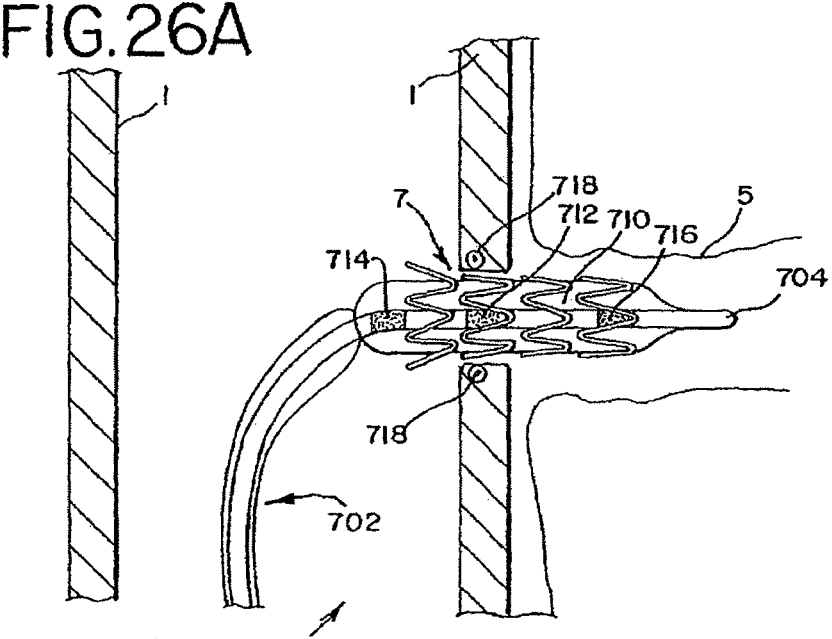
FIGS. 26A-E illustrate a balloon catheter deployment system, including a positional indicator system, that may be used to deploy a branch vessel prosthesis.
Figure 26B:
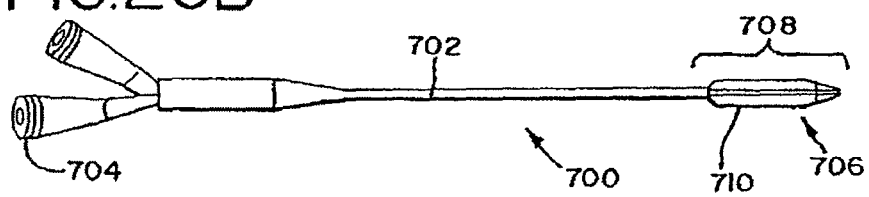
Figure 26C:
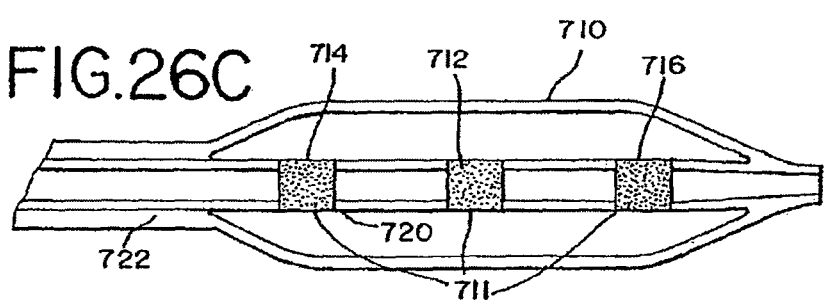
Figure 26D:
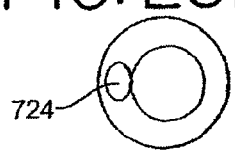
Figure 26E:
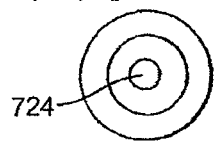

In another aspect, where the branch vessel prosthesis 11 is partially or entirely balloon expandable, a positional indicator system is provided in connection with a balloon delivery system for implanting the branch vessel prosthesis 11, as shown in FIGS. 26A-E. As shown in FIG. 26B, the delivery system 700 used to place and deploy the branch vessel prosthesis 11 comprises a balloon catheter 702 having a proximal portion 704 and a distal portion 706. As used with reference to the delivery catheter 702, the term "proximal" refers to the direction or position closest to the user and the term "distal" refers to the direction or position farthest from the user. The balloon catheter further includes a stent-loading area 708 located on a distal portion 706 of the catheter 702. The stent-loading area 708 comprises a balloon 710 and a positional indicator system 711. The positional indicator system includes one or more positional indicators that correspond with various parts of the of the branch vessel prosthesis 11. For example, the positional indicator system may include a first positional indicator 712 on the catheter that corresponds with that part of the branch vessel prosthesis 11 that is intended to align with the fenestration 7 of the aorta stent graft 1. The system may further include positional indicators 714, 715 that correspond with the proximal distal ends of a branch vessel prosthesis 11.

Preferably the positional indicators are shaped so as to indicate position and orientation of the branch vessel prosthesis during and after deployment. The positional markers may be of any configuration to facilitate their visualization.

For example, the positional markers may be v-shaped with one leg longer than the other.

In a preferred embodiment, the positional indicator system may include a first positional indicator 714 for indicating the position of the proximal end of the branch vessel prosthesis 11 during deployment, a second positional indicator 716 associated with the branch vessel prosthesis 11 for indicating the position of a distal end of the branch vessel prosthesis 11 during deployment, a third positional indicator 712 associated with the branch vessel prosthesis 11 for indicating the position of a point along the branch vessel prosthesis 11 predetermined for optimal alignment with the fenestration 7 during deployment. The system 711 can also include a fourth positional indicator 718 on the aorta stent graft 1 indicating the position of the fenestration 7. At least first, second and third positional indicators also may located on the branch vessel prosthesis 11, as previously described, and are shaped so as to indicate position and orientation of the branch vessel prosthesis 11 during and after deployment.

In operation, the branch vessel prosthesis 11 is positioned about the balloon on the catheter and crimped thereto so that desired portions of the branch vessel prosthesis 11 align with the corresponding positional indicators of the positional indicator system 711. The marker system 711 may be placed on a wire guide lumen 720 or an inflation lumen 722 of the balloon catheter. The balloon may comprise a see-through material so that the marker system 711 can be viewed therethrough to facilitate the placement of the branch vessel prosthesis 11 in the loading area. In one variation shown in FIGS. 26D-E, the balloon catheter may comprise a multi-lumen balloon catheter having a support lumen 724 having a flaring portion through which a mandril (not shown) extends. The mandril stops proximally of the balloon. The mandril provides support to the delivery catheter 702. The mandril may comprise a tapered wire.

The delivery system may also include a balloon expansion catheter 800 that is configured to expand a branch vessel prosthesis of the various configurations described herein having a flaring portion 802 and a tubular portion 804. As shown in FIG. 27A, a delivery catheter 800 may comprise multiple balloons 806, 808. Preferably, the first balloon 806 may be sized and adapted to flare the flaring portion 804 of a branch vessel prosthesis 11, as described herein, and the second balloon 808 may be sized and to adapted expand a tubular portion of a branch vessel prosthesis, as described herein. Accordingly, the balloons may have different compliances.

As shown in 27A, the balloons 806, 808 may be positioned on a branch vessel prosthesis loading area 810 such that the when the branch vessel stent graft 11 is mounted on the stent-loading area 810, the tubular portion 804 of the branch vessel stent graft 11 aligns with the first balloon 806 and the flaring portion 802 of the branch vessel stent graft 11 that is configured to align with the fenestration 7 of the aorta stent graft 1 is aligned with the second balloon 808.

In one embodiment, the balloon catheter carrying the balloons 806, 808 is introduced into the lumen of the aorta stent graft (not shown). The first balloon 806 is aligned substantially with the flaring portion 802 of the branch vessel stent graft 11 and the second balloon 808 is aligned substantially with the tubular portion 806 and the balloons are inflated, as shown in FIG. 27B. The balloons 806, 808 may be inflated simultaneously so as to simultaneously expand the tubular portion and flare the flaring portion. Alternatively, the balloons 806, 808 may be sequentially inflated. In one embodiment, the second balloon 808 is inflated before the first balloon 806, thereby expanding the tubular section 804 before flaring the flaring portion 802. Alternatively, the first balloon 806 may be inflated first. The catheter may be adapted such that the balloons may be inflated independently of each other. The first balloon 806 may be constructed of a semi-compliant (or non-compliant) material and the second balloon 808 may be constructed of a compliant material.

Figure 27C:
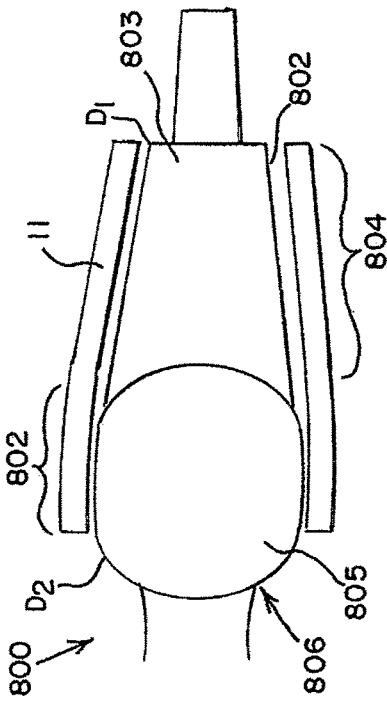
Figure 27D:
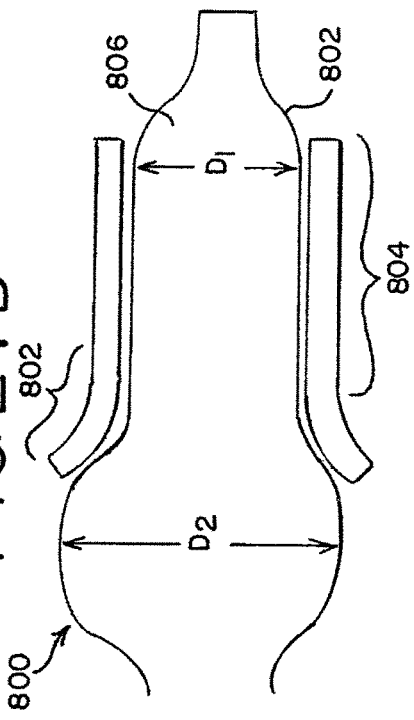
Figure 27A:
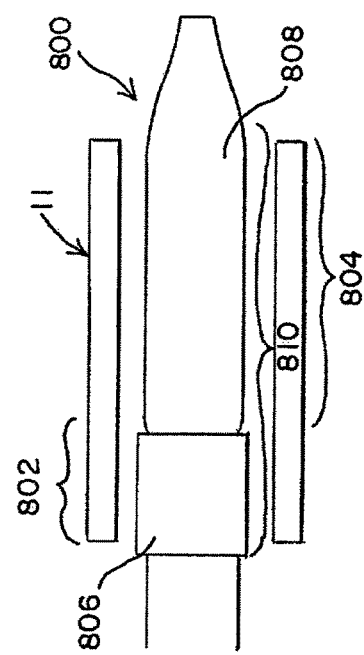
Figure 27B:
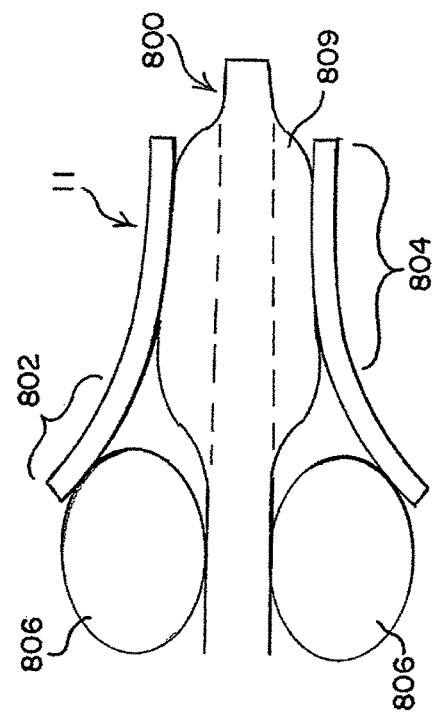

In an alternative configuration, shown in FIG. 27C the delivery catheter 800 may have a single balloon 806 having a first portion 803 for expanding the tubular portion 804 and a second portion 805 for expanding the flaring portion 802 of the branch vessel prosthesis 11. As shown in FIG. 27D, the inflated diameter $D_1$ of the first portion 803 may be smaller than the inflated diameter $D_2$ of the second portion 805.

In another variation, shown in FIGS. 27E-F, the balloon 806 includes a first portion 803, a second portion 805, and a third portion 807, with the first portion 803 for expanding the tubular portion 804 and a second portion 805 for expanding the flaring portion 802 of the branch vessel prosthesis 11. The third portion 807 of the balloon 806 is sized and configured to align with that part of the branch vessel prosthesis 11 that aligns with the fenestration 7 of the aorta stent graft 1. As shown in 27E, the first portion 803 and the second portion 805 may have substantially the same diameter $D_1$. The third portion 807 may have a diameter $D_2$ smaller than the diameter $D_1$ of the first and second portions 803, 805. Alternatively, as shown in FIG. 28F, the diameter $D_1$ of the first portion 803 may be smaller than the diameter $D_2$ of the second portion 805 and greater than the diameter $D_3$ of the third portion 807.

The balloon 806 may also have multiple layers that extend over the balloon length as shown in FIG. 27G-H. For example, the multi-layer balloon 806 may include an inner layer 810 and an outer layer 812. The inner and outer layers 810, 812 may be of different compliancy. The inner layer 810 may be less compliant than the outer layer 812. For example, the inner layer 810 may be constructed of a semi-compliant or noncompliant material, and the outer layer 812 may be constructed of a compliant material. To expand and flare the branch vessel prosthesis 11 with this embodiment, the inner layer may be inflated to expand the branch vessel prosthesis 11. Subsequently or simultaneously, the outer layer 812 may be inflated to expand or flare the flaring portion 814, which is not constrained by the branch vessel 5, of the branch vessel stent graft 814.

In each of the embodiments described, the balloon catheter may be the same as the branch vessel prosthesis introducer or it may be a separate device. In addition, the balloon catheter may comprise a monorail system or rapid-exchange type system. The balloons described may be inflated in any manner known to one of skill in the art. For example, the delivery catheter may include a lumen having a port that exits into the balloon for delivering an inflation fluid to the balloon. When two balloons are present, the delivery catheter may include a first fluid delivery lumen and port for inflation of one balloon and a second fluid delivery lumen and port for inflation of the other balloon. Alternatively, a single lumen may be used that has two ports and a valve for alternating delivery of fluid to the two ports.

Deployment

The branch vessel prosthesis can be deployed in any method known in the art, preferably, the method described in WO 98/53761 in which the device is inserted by an introducer via a surgical cut-down into a an artery, and then advanced into the desired position over a stiff wire guide using endoluminal interventional techniques. For example, a guide wire (not shown) is first introduced into an artery of the patient and advanced until its tip is beyond the desired deployment region the aortic stent graft 1. At this stage, the introducer assembly 500 is fully assembled, and ready for introduction into the patient.

Referring to the components of FIG. 23 and FIGS. 5A-C, the branch vessel prosthesis 11 is retained at one end by the cylindrical sleeve 520 and the other by a proximal attachment section 536, and compressed by the sheath 532. Because the branch vessel prosthesis 11 is mounted on the delivery system in the opposite direction (i.e., the distal end is retained in the cylindrical sleeve and the proximal end is retained in what was previously referred to as the distal attachment section 536), various of the components referred to previously with regard to the introduction system for the aorta stent graft 1 are referred to here as distal rather than proximal and proximal rather than distal.

If the branch vessel prosthesis is to be placed in a branch vessel of the abdominal or thoracic aortic arteries, the introducer assembly 500 can be inserted through a femoral artery over the guide wire, and positioned by radiographic techniques, which are not discussed here.

Once the introducer assembly 500 is in the desired deployment position, the sheath 532 is withdrawn to just proximal of the distal attachment section 536. This action releases the middle portion of the branch vessel prosthesis 11 so that it can expand radially. The distal end of the 32 of the branch vessel prosthesis, for example as shown in FIG. 4A, however, is still retained within the cylindrical sleeve 520 (the end cap as shown in FIG. 25B). Also, the proximal end 30 of the branch vessel prosthesis 11 is still retained within the external sheath 532.

Next, the pin vise 550 is released to allow small movements of the thin walled tube 524 with respect to the thick walled tube 530. These movements allow the prosthesis 11 to be lengthened or shortened or rotated or compressed for accurate placement in the desired location within the lumen. Positional indicators, such as X-ray opaque or radio markers (not shown) may be placed along the branch vessel prosthesis 11 to assist with placement of the prosthesis.

When the distal end of the branch vessel prosthesis 11 is in place in branch vessel, the distal trigger wire is withdrawn by movement of the distal wire release mechanism 540. The distal wire release mechanism 540 and the distal trigger wire can be completely removed by passing the distal wire release mechanism 540 over the pin vise 550, the screw cap 550, and the connection means 526.

Next, the screw cap 550 of the pin vise 540 is then loosened. After this loosening, the thin walled tube 524 can be pushed in a distal direction to move the cylindrical sleeve 530 in a distal direction. When the 520 no longer surrounds a barbed self-expanding stent (such as 40 in Figure A), the self-expanding stent expands. When the self-expanding stent expands, the barbs 42 grip the walls of the lumen to hold the proximal end of the prosthesis 11 in place. From this stage on, the proximal end of the prosthesis 11 typically cannot be moved.

Once the tubular portion 33 has been placed in the branch vessel and the distal end of the branch vessel prosthesis 11 is anchored, the external sheath 432 is withdrawn to proximal of the proximal attachment section 536. This withdrawal releases the flaring portion 36 of the branch vessel prosthesis 11 within the aorta stent graft lumen. Upon release the flaring portion 36, if it is constructed of self expanding material, flares and secures the flaring portion within the lumen of the aorta-stent graft 11. Thereafter, either or both the flaring portion 36 and the tubular portion 33 may be expanded or further expanded by one or more balloons. Alternatively, the prosthesis may be delivered by way of one of the balloon catheters described previously herein.

Throughout this specification various indications have been given as to the scope of the invention but the invention is not limited to any one of these but may reside at two or more of these combined together. It is therefore intended that the foregoing detailed description be regarded as illustrative rather than limiting, and that it be understood that it is the following claims, including all equivalents, that are intended to define the spirit and scope of this invention.

The invention claimed is:

1. A stent graft system for intraluminal deployment in an aorta and a branch vessel comprising:
    an aorta stent graft with a fenestration configured to be aligned with a branch vessel;
    a branch vessel prosthesis having proximal and distal ends, and further having a flaring portion, a tubular portion, and a bending portion disposed between the flaring portion and the tubular portion, wherein, when deployed, the flaring portion is retained within the aorta stent graft, and the tubular portion is configured to extend through the fenestration and into the branch vessel; and
    a first positional indicator positioned at and indicating the bending portion, between the tubular portion and the flaring portion of the branch vessel prosthesis, wherein the first positional indicator aligns with the fenestration during deployment,
    wherein the branch vessel prosthesis comprises an undeployed state prior to flaring of the flaring portion, and further comprises a deployed state in which the flaring portion is flared outward relative to the tubular portion,
    wherein the bending portion comprises at least two alternating strut segments joined by a bend, and the first positional indicator is disposed at the bend between the two strut segments.

2. The system of claim 1 further comprising a second positional indicator on the aorta stent graft indicating the position of the fenestration.

3. The system of claim 2 further comprising a third positional indicator associated with the branch vessel prosthesis for indicating the position of the distal end of the branch vessel prosthesis during deployment.

4. The system of claim 3 further comprising a fourth positional indicator associated with the branch vessel prosthesis for indicating the position of the proximal end of the branch vessel prosthesis.

5. The system of claim 1 wherein the first positional indicator is located on the branch vessel prosthesis.

6. The system of claim 1 wherein the first positional indicator comprises a radiopaque material.

7. The system of one of claim 1, 2, 3, or 4 wherein at least one of the positional indicators is shaped so as to indicate position and orientation of the branch vessel prosthesis.

8. The system of one of claim 1, 2, 3, or 4 wherein at least one of the positional indicators is v-shaped with one leg longer than the other.

9. The stent graft system of claim 1 wherein the first positional indicator is disposed at a location just distal to the flaring portion.

10. The stent graft system of claim 1 wherein the bending portion comprises a "V" shaped-segment in the undeployed state, and wherein the first positional indicator is positioned within a vertex of the "V" shaped-segment.

11. The stent graft system of claim 1 wherein the bending portion comprises one of a "V" shaped-segment, a "W" shaped-segment, and an "S" shaped-segment in at least the undeployed state.

12. A stent graft system for intraluminal deployment in an aorta and a branch vessel comprising:
- an aorta stent graft with a fenestration configured to be aligned with a branch vessel;
- a branch vessel prosthesis having proximal and distal ends, and further having a flaring portion, a tubular portion, and a bending portion disposed between the flaring portion and the tubular portion, wherein, when deployed, the flaring portion is retained within the aorta stent graft, and the tubular portion is configured to extend through the fenestration and into the branch vessel; and
- an introducer configured to deploy the branch vessel prosthesis,
- wherein a first positional indicator is disposed on the introducer at the location of, and indicating the position of, the bending portion of the branch vessel prosthesis that aligns with the fenestration during deployment,
- wherein the branch vessel prosthesis comprises an undeployed state prior to flaring of the flaring portion, and further comprises a deployed state in which the flaring portion is flared outward relative to the tubular portion, and
- wherein the first positional indicator indicates a bending portion of the branch vessel prosthesis that comprises one of a "V" shaped-segment, a "W" shaped-segment, and an "S" shaped-segment in at least the undeployed state.

13. The system of claim 12 further comprising a second positional indicator on the introducer, wherein the second positional indicator indicates the proximal end of the branch vessel prosthesis.

14. The system of claim 13 further comprising a third positional indicator on the introducer, wherein the third positional indicator indicates the position of the tubular portion of the branch vessel prosthesis.

15. The system of claim 14 further comprising a fourth positional indicator on the introducer, wherein the fourth positional indicator indicates the distal end of the branch vessel prosthesis.

16. A stent graft system for intraluminal deployment in an aorta and a branch vessel comprising:
- an aorta stent graft with a fenestration configured to be aligned with a branch vessel;
- a branch vessel prosthesis having proximal and distal ends, and further having a flaring portion, a tubular portion, and a bending portion disposed between the flaring portion and the tubular portion, wherein, when deployed, the flaring portion is retained within the aorta stent graft, and the tubular portion is configured to extend through the fenestration and into the branch vessel; and
- a delivery system comprising a balloon catheter having a balloon configured to deploy the branch vessel prosthesis,
- wherein the balloon catheter comprises a first positional indicator disposed at the location of, and indicating the position of, the bending portion of the branch vessel prosthesis that aligns with the fenestration during deployment,
- wherein the branch vessel prosthesis comprises an undeployed state prior to flaring of the flaring portion, and further comprises a deployed state in which the flaring portion is flared outward relative to the tubular portion, and
- wherein the first positional indicator indicates a bending portion of the branch vessel prosthesis that comprises one of a "V" shaped-segment, a "W" shaped-segment, and an "S" shaped-segment in at least the undeployed state.

17. The system of claim 16 further comprising a second positional indicator on the balloon catheter, wherein the second positional indicator indicates the proximal end of the branch vessel prosthesis.

18. The system of claim 17 further comprising a third positional indicator on the balloon catheter, wherein the third positional indicator indicates the distal end of the branch vessel prosthesis.

* * * * *